US012807554B2

(12) United States Patent
Roettger et al.

(10) Patent No.: US 12,807,554 B2
(45) Date of Patent: Nov. 24, 2026

(54) PROCESS FOR WORKUP OF A METHANOL/WATER MIXTURE IN THE PRODUCTION OF ALKALI METAL METHOXIDES IN A REACTION COLUMN

(71) Applicant: EVONIK OPERATIONS GMBH, Essen (DE)

(72) Inventors: Dirk Roettger, Cologne (DE); Moritz Schröder, Münster (DE); Niklas Paul, Marl (DE); Armin Matthias Rix, Marl (DE); Philip Zitzewitz, Haltern am See (DE); Martin Oldemeyer, Haltern am See (DE); Martin Wüller, Marl (DE); Tanita Valèrie Six, Dortmund (DE); Johannes Ruwwe, Hanau (DE)

(73) Assignee: Evonik Operations GmbH, Essen (DE)

( * ) Notice: Subject to any disclaimer, the term of this patent is extended or adjusted under 35 U.S.C. 154(b) by 511 days.

(21) Appl. No.: 18/570,519

(22) PCT Filed: Mar. 23, 2022

(86) PCT No.: PCT/EP2022/057591
§ 371 (c)(1),
(2) Date: Dec. 14, 2023

(87) PCT Pub. No.: WO2022/263032
PCT Pub. Date: Dec. 22, 2022

(65) Prior Publication Data

US 2024/0279145 A1 Aug. 22, 2024

(30) Foreign Application Priority Data

Jun. 16, 2021 (EP) .................................... 21179722

(51) Int. Cl.
*C07C 29/80* (2006.01)
*B01D 3/00* (2006.01)
(Continued)

(52) U.S. Cl.
CPC ............ *C07C 29/705* (2013.01); *B01D 3/007* (2013.01); *B01D 3/009* (2013.01); *B01D 3/143* (2013.01);
(Continued)

(58) Field of Classification Search
CPC ....... C07C 29/705; C07C 29/80; C07C 31/04; C07C 31/30; B01D 3/007; B01D 3/009; B01D 3/143
See application file for complete search history.

(56) References Cited

U.S. PATENT DOCUMENTS

| | | | |
|---|---|---|---|
| 1,910,331 | A | 5/1933 | Halbig |
| 2,295,256 | A | 9/1942 | Brugma |

(Continued)

FOREIGN PATENT DOCUMENTS

| | | |
|---|---|---|
| CA | 1242309 | 9/1988 |
| CN | 105218315 | 1/2016 |

(Continued)

OTHER PUBLICATIONS

CN 105218315A (Wu et al.; IDS reference; English language machine translation) (Year: 2015).*
(Continued)

*Primary Examiner* — Amy C Bonaparte
*Assistant Examiner* — Derek Rhoades
(74) *Attorney, Agent, or Firm* — Law Office of: Michael A. Sanzo, LLC

(57) ABSTRACT

The present invention relates to a process for workup of a methanol/water mixture which is employed in the production of alkali metal methoxides in a reaction column. The
(Continued)

Figure 1:
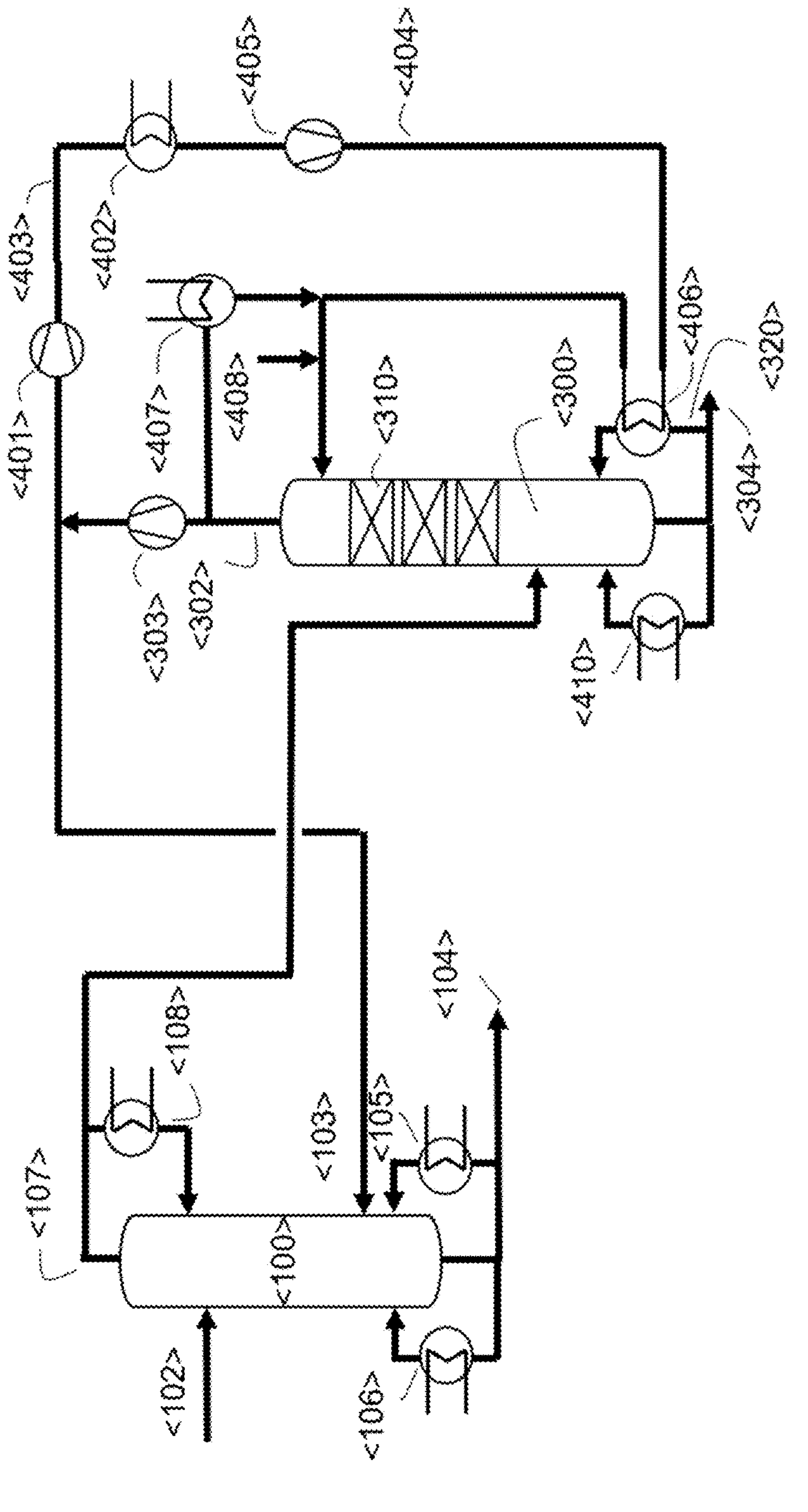

mixture is distillatively separated in a rectification column. The vapours obtained at the upper end of the rectification column are compressed in at least two stages and the energy of the vapours compressed in each case is advantageously transferred to bottoms and side streams of the rectification column. This allows particularly energy-efficient use of the energy of the compressed vapours in the process according to the invention.
The process for workup of a methanol/water mixture is employed in the production of alkali metal methoxides in a reaction column, wherein methanol and alkali metal hydroxide solution are reacted with one another in countercurrent in a reaction column. Alkali metal methoxide dissolved in methanol is withdrawn at the lower end and a methanol/water mixture which is worked up with the workup process according to the invention is withdrawn at the upper end. The energy of the compressed vapours may additionally be used for operating the reaction column or for operating a reaction column in which a process for transalcoholization of alkali metal alkoxides is performed.

20 Claims, 10 Drawing Sheets

(51) Int. Cl.

| | |
|---|---|
| ***B01D 3/14*** | (2006.01) |
| ***C07C 29/70*** | (2006.01) |
| ***C07C 31/04*** | (2006.01) |
| ***C07C 31/30*** | (2006.01) |

(52) U.S. Cl.
CPC .............. *C07C 29/80* (2013.01); *C07C 31/04* (2013.01); *C07C 31/30* (2013.01)

(56) References Cited

U.S. PATENT DOCUMENTS

| | | | |
|---|---|---|---|
| 2,877,274 | A | 3/1959 | Kramis |
| 3,418,383 | A | 12/1968 | Lenz et al. |
| 4,327,230 | A | 4/1982 | Ackermann et al. |
| 4,566,947 | A | 1/1986 | Tsuruta |
| 4,895,989 | A | 1/1990 | Sander et al. |
| 6,759,560 | B2 | 7/2004 | Guth et al. |
| 7,847,133 | B2 | 12/2010 | Ruwwe et al. |
| 8,069,687 | B2 | 12/2011 | Jork et al. |
| 11,174,559 | B2 | 11/2021 | Horn et al. |
| 11,634,372 | B2 | 4/2023 | Roettger et al. |
| 11,661,388 | B2 | 5/2023 | Roettger et al. |
| 11,746,075 | B2 | 9/2023 | Roettger et al. |
| 11,945,767 | B2 | 4/2024 | Weissker et al. |
| 12,180,141 | B2 | 12/2024 | Roettger et al. |
| 2008/0296786 | A1* | 12/2008 | Ruwwe et al. ........... C07F 1/00 260/665 |
| 2011/0313207 | A1 | 12/2011 | Kaibel et al. |
| 2020/0148706 | A1 | 5/2020 | Sakurai et al. |
| 2022/0340508 | A1 | 10/2022 | Roettger et al. |
| 2022/0340509 | A1 | 10/2022 | Roettger et al. |
| 2024/0308942 | A1 | 9/2024 | Roettger et al. |

FOREIGN PATENT DOCUMENTS

| | | |
|---|---|---|
| DE | 968903 | 4/1958 |
| EP | 122367 | 10/1984 |
| GB | 377631 | 7/1932 |
| GB | 737453 | 9/1955 |
| WO | 2022117803 | 6/2022 |
| WO | WO 2022/263032 | 12/2022 |

OTHER PUBLICATIONS

Copending U.S. Appl. No. 19/121,093, filed Apr. 14, 2025. This application has not yet published, a pdf is enclosed herewith.
Copending U.S. Appl. No. 19/132,848, filed May 26, 2025. This application has not yet published, a pdf is enclosed herewith.
English language translation of the International Search Report for corresponding PCT/EP2022/057591 filed Mar. 23, 2022.
English language translation of the Written Opinion of the International Searching Authority for corresponding PCT/EP2022/057591 filed Mar. 23, 2022.
International Preliminary Report on Patentability for corresponding PCT/EP2022/057591 filed Mar. 23, 2022.
European Search Report and Search Opinion for EP 21179722.0 filed Jun. 16, 2021, corresponding to PCT/EP2022/057591, with partial English language machine translation of the search opinion.
English language translation of the International Search Report for international application PCT/EP2022/051869 filed Jan. 27, 2022, corresponding to copending U.S. Appl. No. 18/275,469.
English language translation of the Written Opinion of the International Searching Authority for international application PCT/EP2022/051869 filed Jan. 27, 2022, corresponding to copending U.S. Appl. No. 18/275,469.
International Preliminary Report on Patentability for international application PCT/EP2022/051869 filed Jan. 27, 2022, corresponding to copending U.S. Appl. No. 18/275,469.
European Search Report for EP 21155473 filed Feb. 5, 2021, corresponding to PCT/EP2022/051869 filed Jan. 27, 2022, with partial English language machine translation of the search opinion.
Translation of Office Action dated Nov. 14, 2022 from Taiwan examination proceeding corresponding to copending U.S. Appl. No. 18/275,469.
Dejanovic, et al., "Dividing wall column—A breakthrough towards sustainable distilling," *Chemical Engineering and Processing* 49(6):559-580 (Jun. 2010).
"Gas/Liquid Separation Technology," (2018); found at http://www.sulzer.com/-/media/files/products/separation-technology/feed-inlet-devices/gas_liquid_technology.ashx?la=en.
U.S. Appl. No. 17/659,086, filed Apr. 13, 2022, US-2022/0340509 A1, Oct. 27, 2022, Roettger.
U.S. Appl. No. 18/275,469, filed Aug. 2, 2023, Roettger.

* cited by examiner

PROCESS FOR WORKUP OF A METHANOL/WATER MIXTURE IN THE PRODUCTION OF ALKALI METAL METHOXIDES IN A REACTION COLUMN

CROSS REFERENCE TO RELATED APPLICATIONS

The present application is US national stage of international application PCT/EP2022/057591, which had an international filing date of Mar. 23, 2022 and which was published on Dec. 22, 2022. The PCT application claims priority to EP 21179722.0, filed on Jun. 16, 2021. The content of these prior filings is hereby incorporated by reference in their entirety.

The present invention relates to a process for workup of a methanol/water mixture which is employed in the production of alkali metal methoxides in a reaction column. The mixture is distillatively separated in a rectification column. The vapours obtained at the upper end of the rectification column are compressed in at least two stages and the energy of the vapours compressed in each case is advantageously transferred to bottoms and side streams of the rectification column. This allows particularly energy-efficient use of the energy of the compressed vapours in the process according to the invention.

The process for workup of a methanol/water mixture is employed in the production of alkali metal methoxides in a reaction column, wherein methanol and alkali metal hydroxide solution are reacted with one another in countercurrent in a reaction column. Alkali metal methoxide dissolved in methanol is withdrawn at the lower end and a methanol/water mixture which is worked up with the workup process according to the invention is withdrawn at the upper end. The energy of the compressed vapours may additionally be used for operating the reaction column or for operating a reaction column in which a process for transalcoholization of alkali metal alkoxides is performed.

1. BACKGROUND OF THE INVENTION

Alcohol/water mixtures are obtained for example in the production of alkali metal alkoxides from aqueous, optionally alcohol-containing, alkali metal hydroxide solution and alcohol. This process employs in particular methanol and ethanol as the alcohol.

Alkali metal alkoxides are used as strong bases in the synthesis of numerous chemicals, for example in the production of pharmaceutical or agrochemical active ingredients. Alkali metal alkoxides are also used as catalysts in transesterification and amidation reactions.

Alkali metal alkoxides (MOR) are produced by reactive distillation of alkali metal hydroxides (MOH) and alcohols (ROH) in a countercurrent distillation column, wherein the water of reaction formed according to the following reaction <1> is removed with the distillate.

$$MOH + ROH \rightleftharpoons MOR + H_2O.$$

Such a process principle is described, for example, in U.S. Pat. No. 2,877,274 A, wherein aqueous alkali metal hydroxide solution and gaseous methanol are run in countercurrent in a reactive rectification column. This process is described again in generally unchanged form in WO 01/42178 A1.

Similar processes, which, however, additionally employ an entraining agent such as benzene, are described in GB 377,631 A and U.S. Pat. No. 1,910,331 A. This entraining agent is used to separate water and the water-soluble alcohol. In both patent specifications the condensate is subjected to a phase separation to separate off the water of reaction. A further similar process is the reaction of an alkali metal alkoxide with another alcohol in a reaction column ("transalcoholization") according to DE 27 26 491 A1.

Correspondingly, DE 96 89 03 C describes a process for continuous production of alkali metal alkoxides in a reaction column, wherein the water-alcohol mixture withdrawn at the top of the column is condensed and then subjected to a phase separation. The aqueous phase is discarded and the alcoholic phase is returned to the top of the column together with the fresh alcohol. EP 0 299 577 A2 describes a similar process, wherein the water in the condensate is separated off with the aid of a membrane.

The most industrially important alkali metal alkoxides are those of sodium and potassium, especially the methoxides and ethoxides. Their synthesis is frequently described in the prior art, for example in EP 1 997 794 A1.

The syntheses of alkali metal alkoxides by reactive rectification described in the prior art typically afford vapours comprising the employed alcohol and water. It is advantageous for economic reasons to reuse the alcohol comprised in the vapours as a reactant in the reactive distillation. The vapours are therefore typically supplied to a rectification column and the alcohol present therein is separated off (described for example in GB 737 453 A and U.S. Pat. No. 4,566,947 A). The thus recovered alcohol is then supplied to the reactive distillation as a reactant for example.

Alternatively or in addition a portion of the alcohol vapour may be utilized for heating the rectification column (described in WO 2010/097318 A1). However, this requires that the vapour be compressed in order to achieve the temperature level required for heating the rectification column. Especially a multistage compression of the vapour is thermodynamically advantageous. The vapour is cooled between the compression stages here. The intermediate cooling also ensures that the maximum allowable temperature of the compressor is not exceeded. The disadvantage of this cooling performed in the customary processes is that the energy thus withdrawn dissipates without being utilized.

There is therefore a need for improved processes for workup of an alcohol/water mixture as employable in particular in the context of a process for producing alkali metal alkoxides. This process shall feature a particularly efficient utilization of the energy present in the compressed vapours for operation of the rectification column. The process shall accordingly allow energy-efficient utilization of the heat liberated during compression and cooling of the vapours.

2. BRIEF SUMMARY OF THE INVENTION

The present invention relates to a process for producing at least one alkali metal alkoxide of formula $M_AOR$, wherein R is methyl, and wherein $M_A$ is a metal selected from sodium, potassium, preferably sodium.

In the process according to the invention for producing at least one alkali metal alkoxide a mixture G comprising water and methanol ROH is obtained which is employed in a process for workup of a mixture G comprising water and alcohol ROH, wherein R is methyl, and is worked up using the process for workup of a mixture G. The process for workup of a mixture G is performed in a rectification column and is accordingly a distillative process.

In a further, preferred aspect the present invention relates to a process for transalcoholization of alkali metal alkoxides. In this process the alcohol of an alkali metal alkoxide $M_cOR'$ is substituted by another alcohol R"OH by reacting $M_cOR'$ with R"OH in a reaction column to afford $M_cOR"$, wherein the process utilizes energy from certain vapour streams from the process according to the invention for workup of a mixture G for operation.

3. FIGURES

3.1 FIG. 1

FIG. 1 shows a noninventive embodiment of a process for producing alkali metal methoxides in which the distillative separation of the methanol-water mixture is carried out as in the prior art (WO 2010/097318 A1, FIG. 1).

Aqueous NaOH $S_{AE2}$ <102> is reacted in a reaction column $RR_A$ <100> with methanol $S_{AE1}$ <103> to afford the corresponding sodium alkoxide. At the top of the reaction column $RR_A$ <100> an aqueous NaOH solution is added as reactant stream $S_{AE2}$ <102>. It is alternatively also possible to add a methanolic NaOH solution as reactant stream $S_{AE2}$ <102>. To produce the corresponding potassium methoxide aqueous or methanolic KOH solution is added as reactant stream $S_{AE2}$ <102>. Above the bottom of the reaction column $RR_A$ <100> methanol is added in vapour form as reactant stream $S_{AE1}$ <103>.

At the bottom of the reaction column $RR_A$ <100> a mixture of the corresponding methoxide in the methanol $S_{AP*}$ <104> is withdrawn. The bottoms evaporator $V_{SA}$ <105> and the optional evaporator $V_{SA'}$<106> at the bottom of the column $RR_A$ <100> are used to adjust the concentration of the sodium methoxide solution $S_{AP*}$ <104> to the desired value.

At the top of the reaction column $RR_A$ <100> a vapour stream $S_{AB}$ <107> is withdrawn. A portion of the vapour stream $S_{AB}$ <107> is condensed in the condenser $K_{RRA}$ <108> and applied in liquid form to the top of the reaction column $RR_A$ <100> as reflux. However, condenser $K_{RRA}$ <108> and the establishment of the reflux are optional.

The obtained vapour $S_{AB}$ <107> is in whole or in part sent to a rectification column, a water/methanol column, $RD_A$ <300> as mixture G. The rectification column $RD_A$ <300> contains internals <310>. Therein the mixture G is distillatively separated and the methanol is distillatively recovered as vapour $S_{OA}$ <302> overhead.

A reflux may be established at the rectification column $RD_A$ <300>. In this case a portion of the vapour $S_{OA}$ <302> is condensed in a condenser $K_{RD}$ <407> and then recycled into the rectification column $RD_A$ <300>. In the embodiments where no reflux is established the remaining portion of $S_{OA}$ <302>/the complete vapour stream $S_{OA}$ <302> is precompressed using compressor $VD_{AB2}$ <303>. A portion of this precompressed vapour is recycled to the reaction column $RR_A$ <100> where it is employed as reactant stream $S_{AE1}$ <103>.

The remaining portion of $S_{OA}$ <302> is passed to the compressor $VD_x$ <401> where it is further compressed to afford vapour stream $S_{OA1}$ <403>, from which energy may be withdrawn in the optional intermediate cooler $WT_X$ <402>.

The vapour stream $S_{OA1}$ <403> is once again compressed using compressor $VD_x$ <405> and the resulting vapour $S_{OA2}$ <404> is then sent to the evaporator $V_{SRD}$ <406> at the bottom of the rectification column $RD_A$ <300> for heating, after which fresh methanol <408> is optionally added and it is returned to the rectification column $RD_A$ <300> as reflux. If a reflux is established at the rectification column $RD_A$ <300>, the stream $S_{OA2}$ <404> may be mixed with the reflux, i.e. the condensate, from $K_{RD}$ <407> before recycling to $RD_A$ <300>, and fed into $RD_A$ <300> together therewith. Obtained at the bottom of the rectification column $RD_A$ <300> is a water stream $S_{UA}$ <304> which may be at least partially (stream $S_{UA1}$ <320>) recycled to the rectification column $RD_A$ <300>, wherein said stream may be passed through the evaporator $V_{SRD}$ <406> and/or $V_{SRD'}$ <410>.

3.2 FIG. 2

Figure 2:
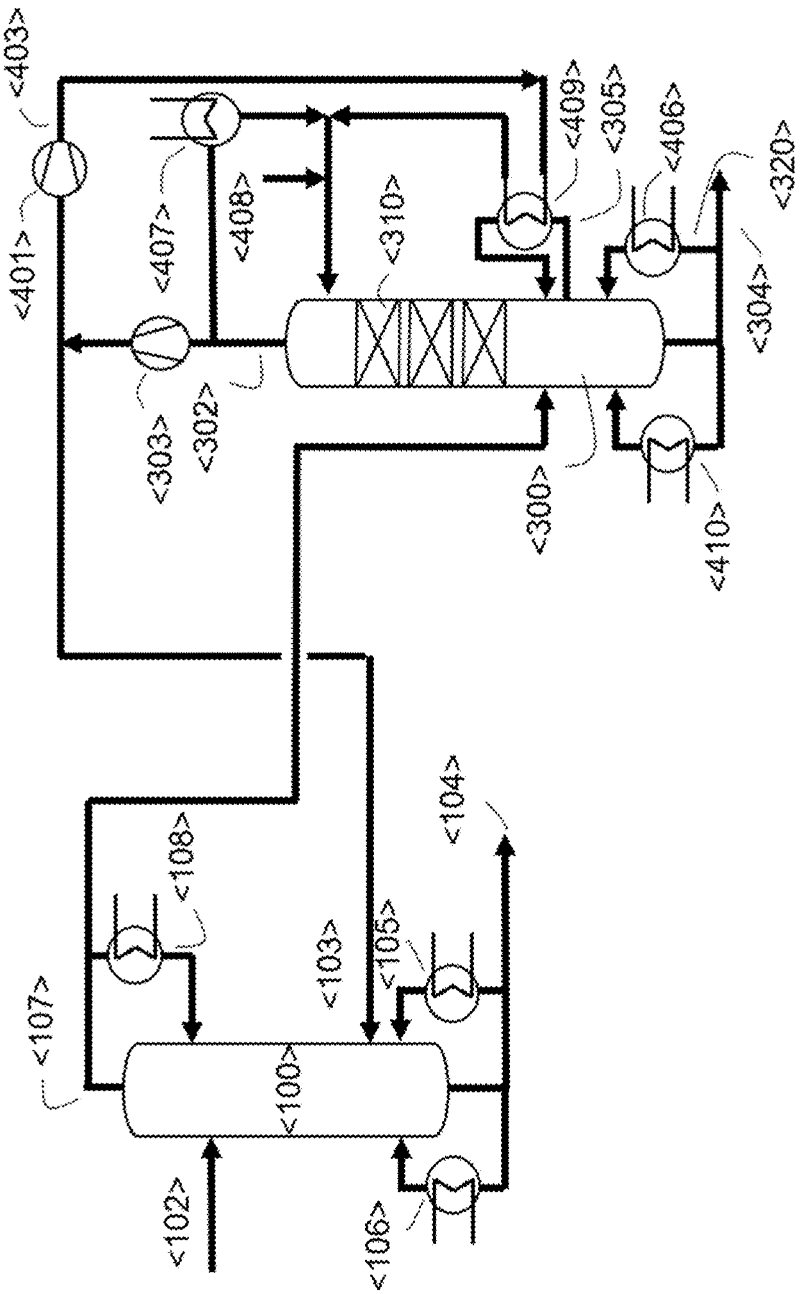

FIG. 2 shows a further noninventive embodiment of a process which corresponds to the embodiment shown in FIG. 2 of WO 2010/097318 A1.

This embodiment corresponds to the one described in FIG. 1 with the following additional/different features: In addition to the evaporators $V_{SRD'}$ <406> and $V_{SRD'}$ <410> the column bottom of the rectification column $RD_A$ <300> comprises an intermediate evaporator $V_{ZRD}$ <409>. A side stream $S_{ZA}$ <305> is withdrawn from the rectification column $RD_A$ <300> and passed through $V_{ZRD}$ <409> before being returned to the rectification column $RD_A$ <300>. A portion of the vapour stream $S_{OA}$ <302> is precompressed using compressor $VD_{AB2}$ <303> and once a portion thereof has been diverted to the reaction column $RR_A$ <100> is compressed in compressor $V_{D1}$ <401> to afford vapour stream $S_{OA1}$ <403> which is sent to the intermediate evaporator $V_{ZRD}$ <409> for heating. Heating in evaporator $V_{SRD}$ <406> or in evaporator $V_{SRD'}$ <410> by $S_{OA1}$ <403> is not carried out. The vapour stream $S_{OA}$ <302> utilized for heating $V_{ZRD}$ <409> is subsequently mixed with the condensate from $K_{RD}$ <407> and the fresh methanol <408> and recycled into the rectification column $RD_A$ <300> as reflux. Separate recycling of the reflux from $S_{OA}$ <302> to the rectification column $RD_A$ <300> is likewise possible.

3.3 FIG. 3

Figure 3:
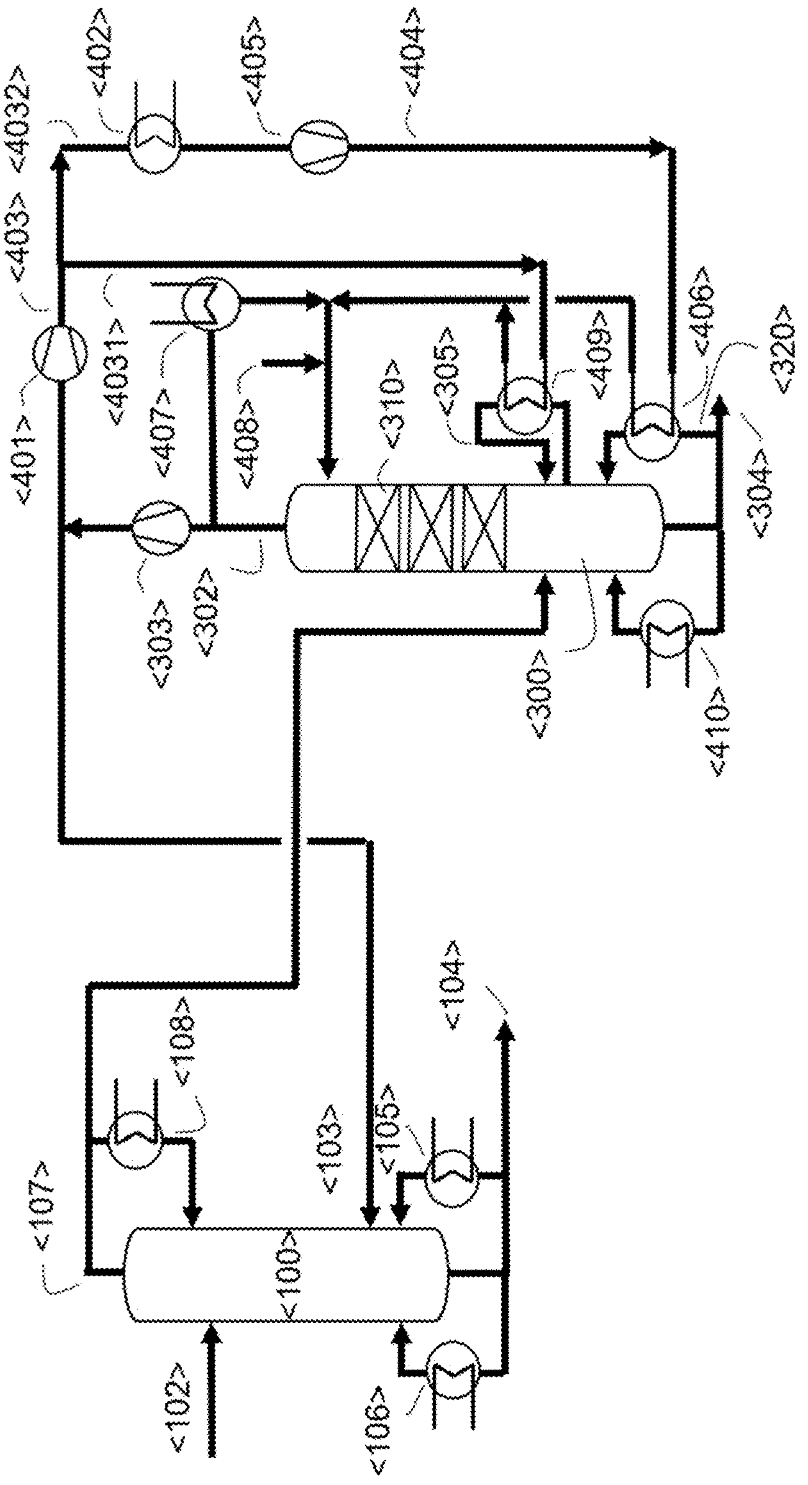

FIG. 3 shows an embodiment of the process according to the invention. This corresponds to the embodiments described in FIGS. 1 and 2. The rectification column $RD_A$ <300> comprises an intermediate evaporator $V_{ZRD}$ <409> and a bottoms evaporator $V_{SRD}$ <406> and optionally the bottoms evaporator $V_{SRD'}$ <410>.

The inventive embodiment has the following differences from the aforementioned embodiments:

1. After compression of a portion of the vapour stream $S_{OA}$ <302> in the compressor $V_{D1}$ <401> the vapour stream $S_{OA1}$ <403> is divided into two portions $S_{OA11}$ <4031> and $S_{OA12}$ <4032>.
2. $S_{OA11}$ <4031> is supplied to the intermediate evaporator $V_{ZRD}$ <409> for heating the stream $S_{ZA}$ <305>.
3. $S_{OA12}$ <4032> is further compressed in the compressor $VD_x$ <405> to afford stream $S_{OA2}$ <404> and $S_{OA2}$ <404> is sent to the bottoms evaporator $V_{SRD}$ <406> for heating the stream $S_{UA1}$ <320>.
4. Once $S_{OA11}$ <4031> and $S_{OA2}$ <404> have left the respective evaporator $V_{ZRD}$ <409>/$V_{SRD}$ <406> they are combined and the combined stream is mixed with the reflux (i.e. the condensate from $K_{RD}$ <407>) and the fresh methanol <408> and recycled into the rectification column $RD_A$ <300>. Separate recycling of these streams to the rectification column $RD_A$ <300> is likewise possible.

These differences have the result that the energy of the vapour $S_{OA1}$ <403> may be more efficiently utilized for heating the rectification column $RD_A$ <300> compared to the embodiments according to FIGS. 1 and 2.

3.4 FIG. 4

Figure 4:
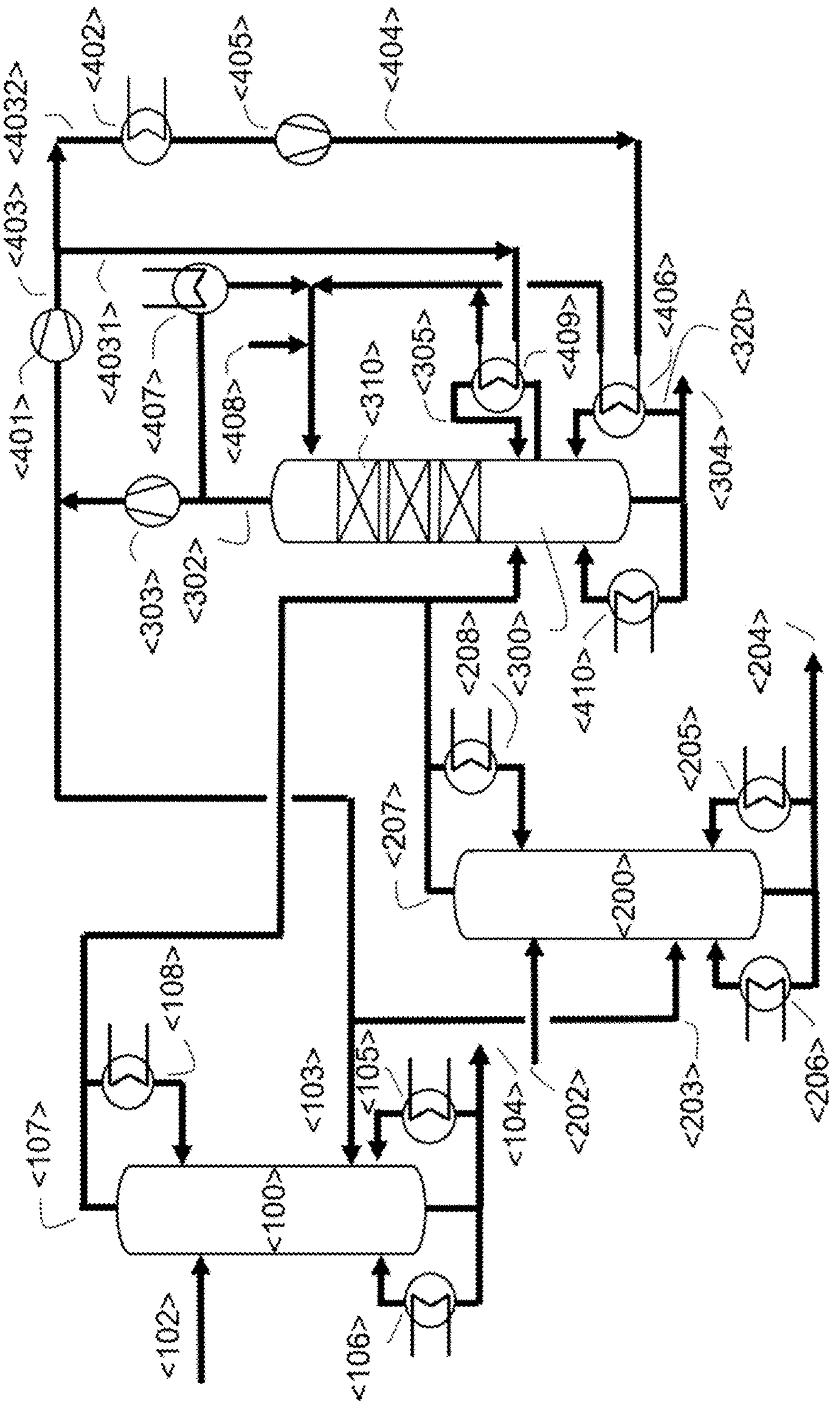

FIG. 4 shows an embodiment of the process according to the invention. This corresponds to the embodiments described in FIG. 3 with the difference that in a second reaction column $RR_B$ <200> an aqueous KOH solution $S_{BE2}$ <202> is reacted with methanol which is also used for reaction in $RR_A$ <100>, $S_{BE1}$ <203> to afford the corresponding potassium methoxide.

At the top of the reaction column $RR_B$ <200> an aqueous KOH solution is added as reactant stream $S_{BE2}$ <202>. It is alternatively possible to also add a methanolic KOH solution as reactant stream $S_{BE2}$ <202>. Above the bottom of the reaction column $RR_B$ <200> methanol is added in vapour form as reactant stream $S_{BE1}$ <203>.

At the bottom of the reaction column $RR_B$ <200> a mixture of the corresponding methoxide in methanol $S_{BP*}$ <204> is withdrawn. The bottoms evaporator $V_{SB}$ <205> and the optional evaporator $V_{SB'}$ <206> at the bottom of the column $RR_B$ <200> are used to adjust the concentration of the potassium methoxide solution $S_{BP*}$ <204> to the desired value.

At the top of the reaction column $RR_B$ <200> a vapour stream $S_{BB}$ <207> is withdrawn. A portion of the vapour stream $S_{BB}$ <207> is condensed in the condenser $K_{RRB}$ <208> and applied in liquid form to the top of the reaction column $RR_B$ <200> as reflux. However, condenser $K_{RRB}$ <208> and the establishment of the reflux are optional.

The obtained vapour $S_{BB}$ <207> is supplied to the rectification column $RD_A$ <300> in admixture with the portion of the vapour $S_{AB}$ <107> not condensed in the condenser $K_{RRA}$ <108>.

A further difference from the embodiment according to FIG. 3 is that the precompressed portion of the vapour $S_{OA}$ <302> is partially recycled to the reaction column $RR_A$ <100> and $RR_B$ <200> where it is used as reactant stream $S_{AE1}$ <103>/$S_{BE1}$ <203>.

3.5 FIG. 5

Figure 5:
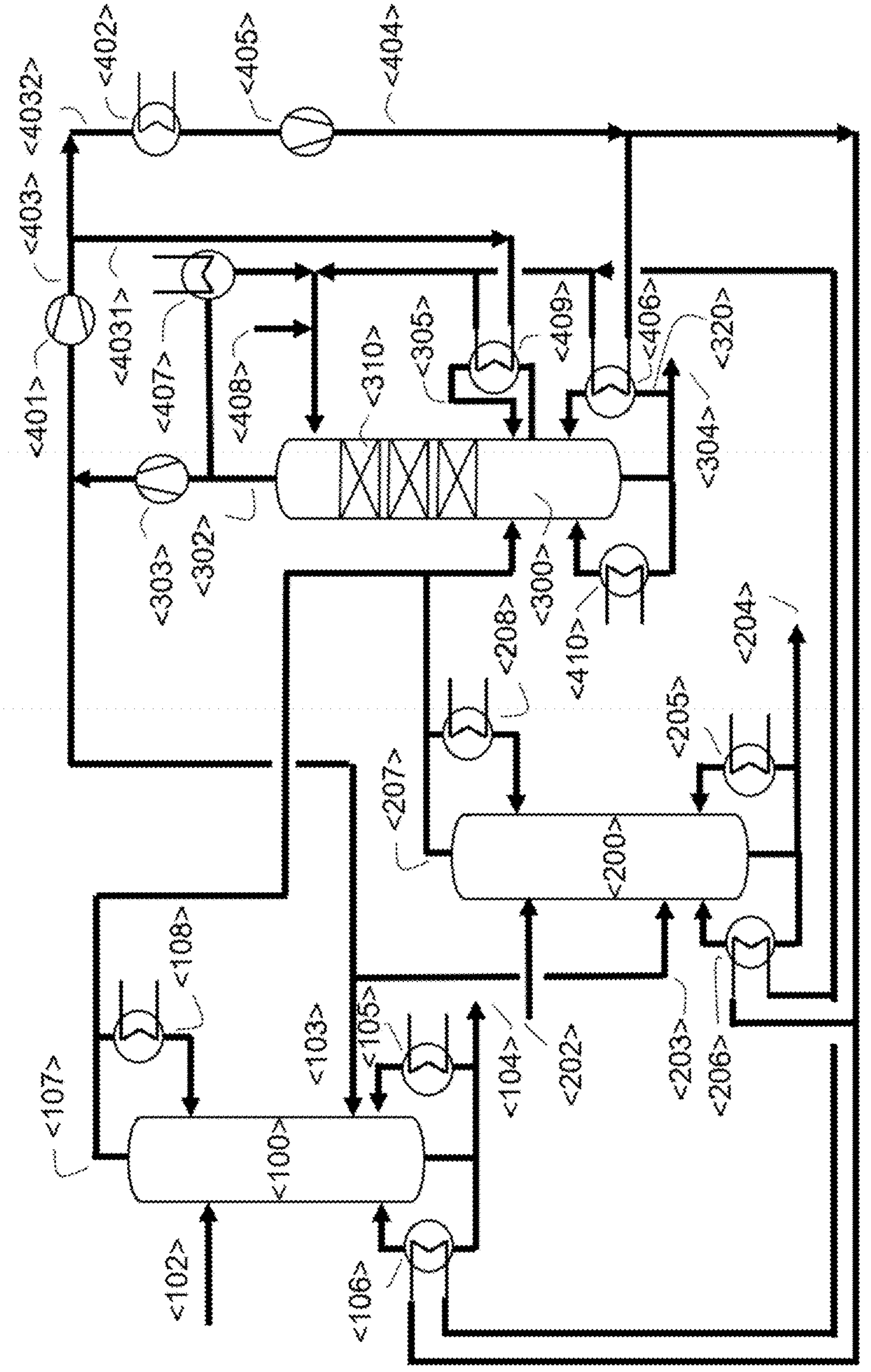

FIG. 5 shows an embodiment of the process according to the invention. This corresponds to the embodiments described in FIG. 4 with the difference that a portion of $S_{OA2}$ <404> is also utilized for heating the evaporator $V_{SA'}$ <106> at the bottom of the column $RR_A$ <100> and the evaporator $V_{SB'}$ <206> at the bottom of the column $RR_B$ <200>.

3.6 FIG. 6

Figure 6:
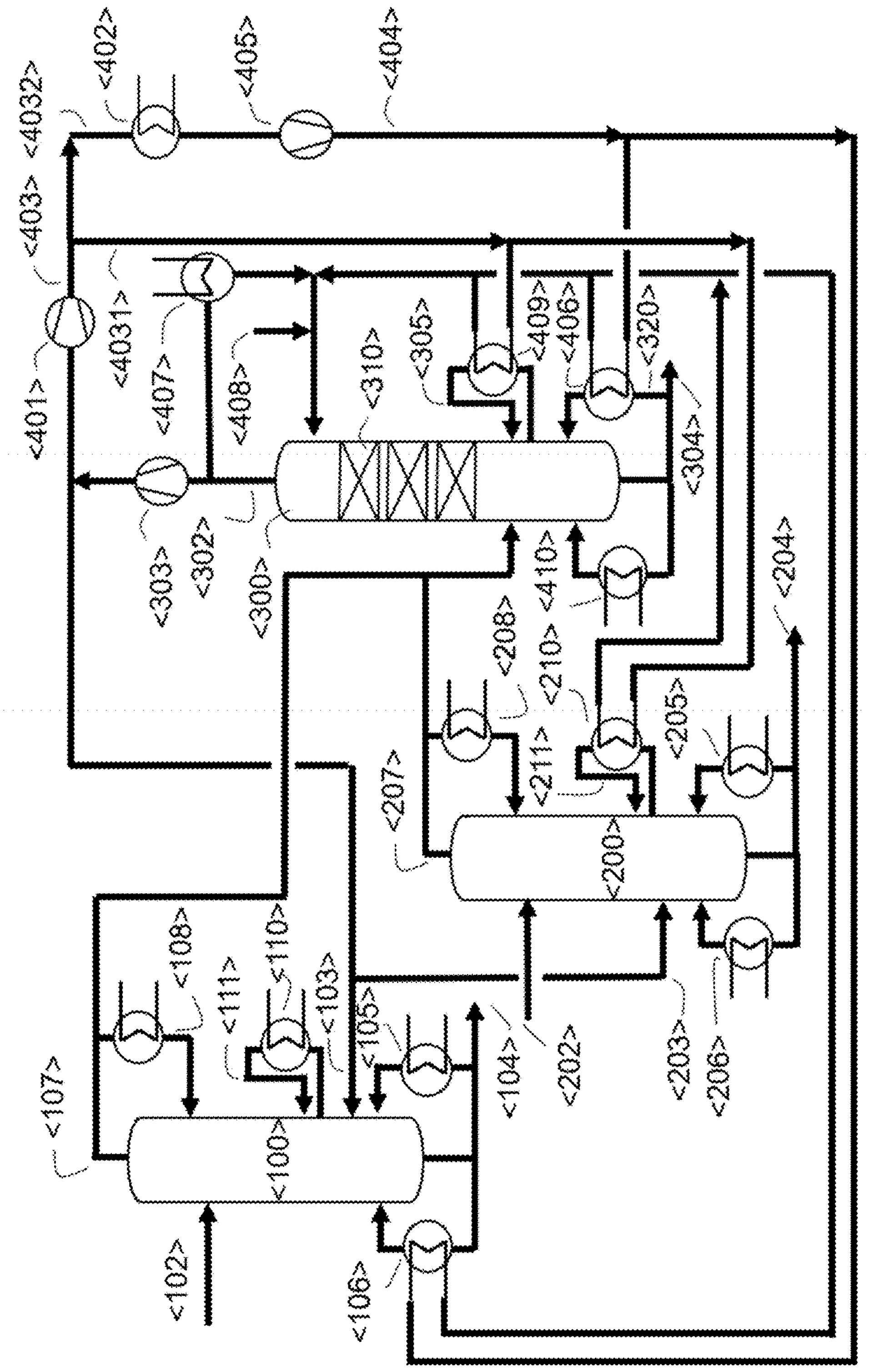

FIG. 6 shows an embodiment of the process according to the invention. This corresponds to the embodiment described in FIG. 5 with the difference that the reaction columns $RR_A$ <100> and $RR_B$ <200> each comprise an intermediate evaporator $V_{ZA}$ <110> and $V_{ZB}$ <210>. A side stream $S_{ZAA}$ <111> is withdrawn from the reaction column $RR_A$ <100> and passed through $V_{ZA}$ <110> before being returned to the reaction column $RR_A$ <100>. A side stream $S_{ZBA}$ <211> is withdrawn from the reaction column $RR_B$ <200> and passed through $V_{ZB}$ <210> before being returned to the reaction column $RR_B$ <200>.

In a departure from FIG. 5 a portion of $S_{OA2}$ <404> is utilized only for heating the evaporator $V_{SA'}$ <106> at the bottom of the column $RR_A$ <100>. A portion of $S_{OA11}$ <4031> is utilized for heating the evaporator $V_{ZB}$ <210> by contrast.

3.7 FIG. 7

Figure 7:
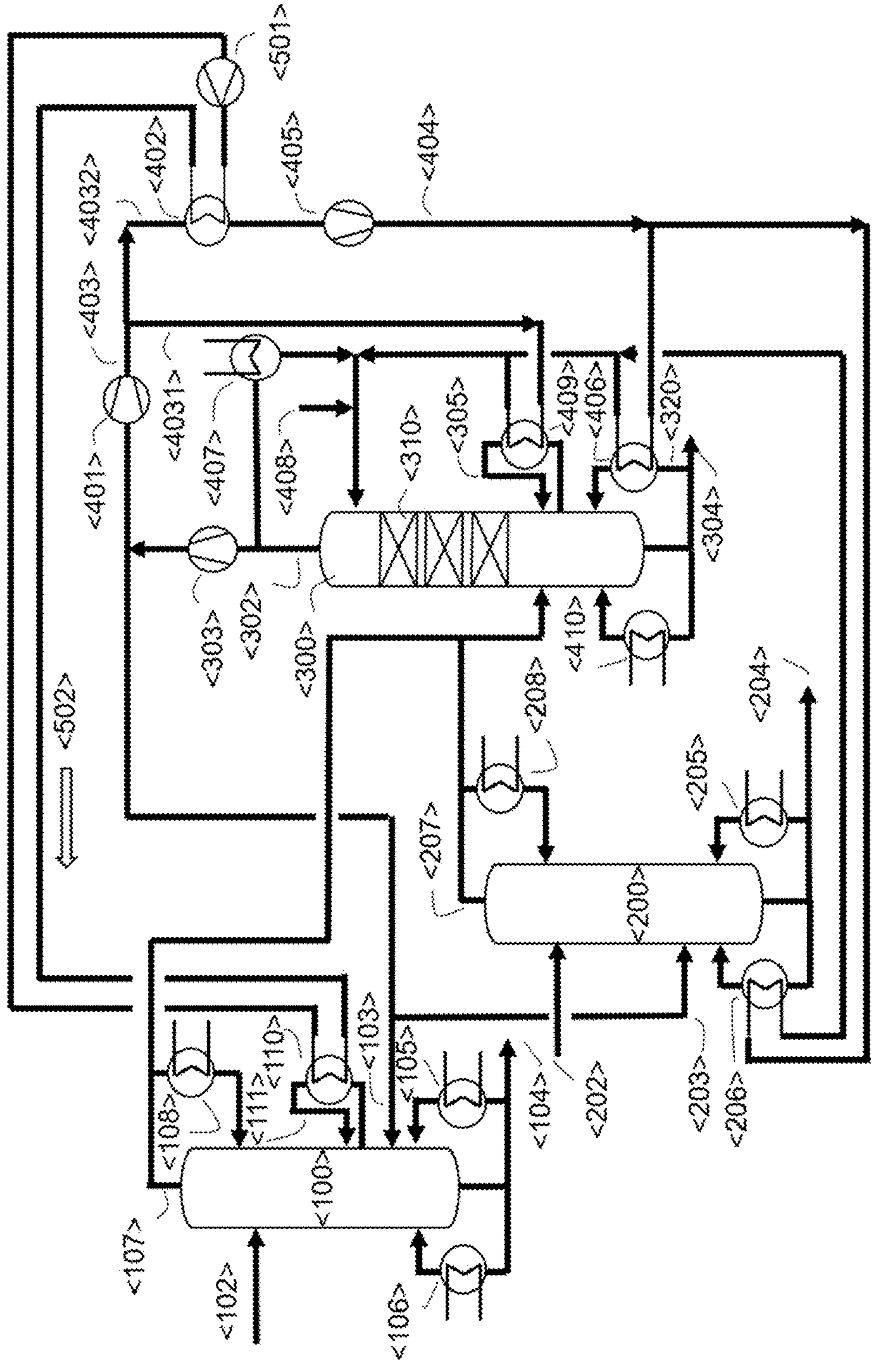

FIG. 7 shows an embodiment of the process according to the invention. This corresponds to the embodiments described in FIG. 5 with the difference that the reaction column $RR_A$ <100> comprises an intermediate evaporator $V_{ZA}$ <110>. A side stream $S_{ZAA}$ <111> is withdrawn from the reaction column $RR_A$ <100> and passed through $V_{ZA}$ <110> before being returned to the reaction column $RR_A$ <100>. In a departure from FIG. 5 a portion of $S_{OA2}$ <404> is employed only for heating the evaporator $V_{SB'}$ <206> at the bottom of the column $RR_B$ <200>. The intermediate evaporator $V_{ZA}$ <110> is heated via a heat transfer medium W <502>, in particular water, transported by a pump <501> which absorbs heat from $S_{OA12}$ <4032> in the intermediate cooler $WT_X$ <402> and releases it in the intermediate evaporator $V_{ZA}$ <110>.

3.8 FIG. 8

Figure 8:
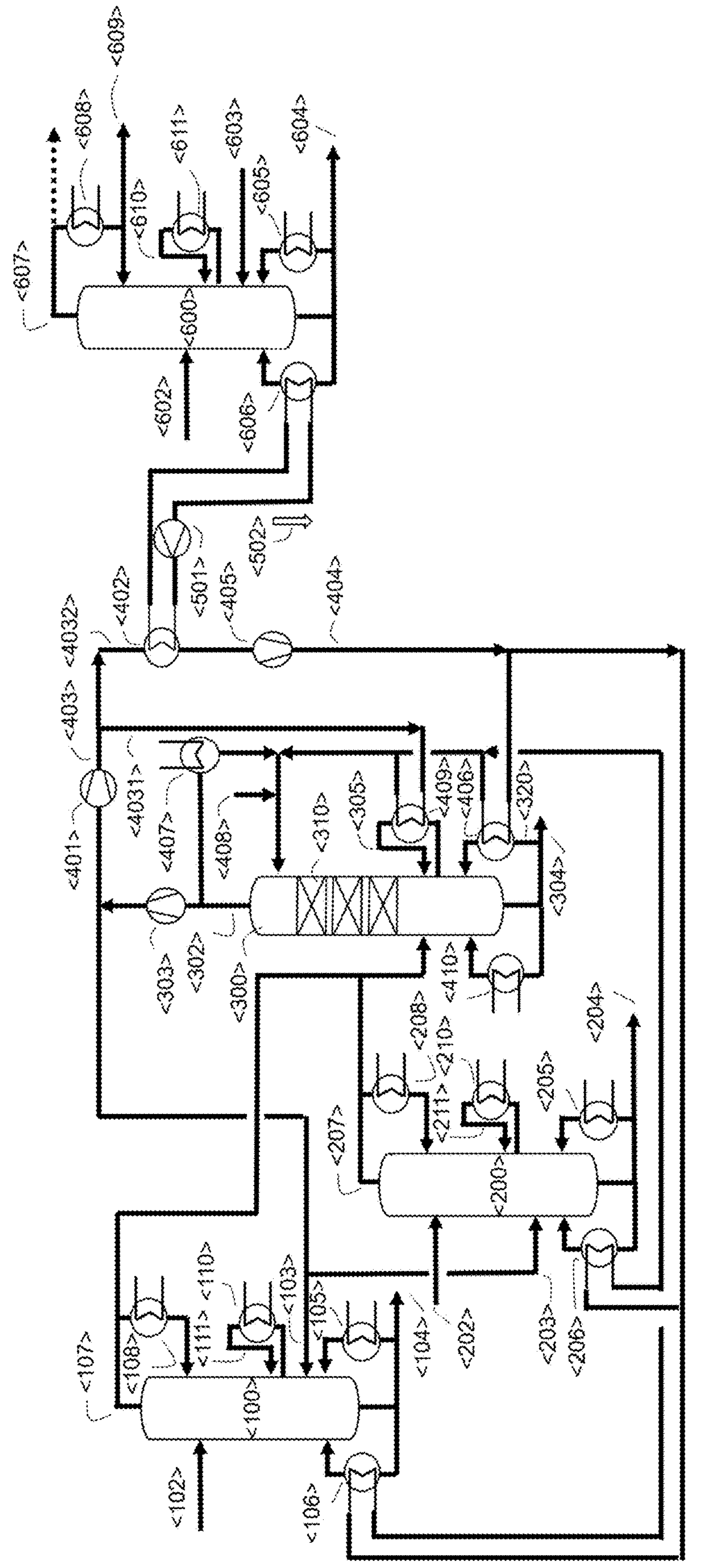

FIG. 8 shows an embodiment of the process according to the invention. This corresponds to the embodiment described in FIG. 5 with the difference that the reaction columns $RR_A$ <100> and $RR_B$ <200> each comprise an intermediate evaporator $V_{ZA}$ <110> and $V_{ZB}$ <210>. A side stream $S_{ZAA}$ <111> is withdrawn from the reaction column $RR_A$ <100> and passed through $V_{ZA}$ <110> before being returned to the reaction column $RR_A$ <100>. A side stream $S_{ZBA}$ <211> is withdrawn from the reaction column $RR_B$ <200> and passed through $V_{ZB}$ <210> before being returned to the reaction column $RR_B$ <200>.

In addition, FIG. 8 shows a further preferred embodiment of the process according to the invention. It shows a reactive rectification column $RR_C$ <600> for transalcoholization of sodium methoxide to sodium ethoxide which is at least partially operated with energy from the stream $S_{OA12}$ <4032>. The column $RR_C$ <600> comprises the bottoms evaporators $V_{SC}$ <605> and $V_{SC}$ <606>.

Sodium methoxide solution $S_{CE1}$ <602> is in a reaction column $RR_C$ <600> reacted in countercurrent with ethanol $S_{CE2}$ <603> to afford sodium ethoxide and this is withdrawn as an ethanolic solution.

Withdrawn at the bottom of the reaction column $RR_C$ <600> is a bottoms product stream $S_{CP}$ <604> comprising sodium ethoxide.

At the top of the reaction column $RR_C$ <600> a vapour stream $S_{CB}$ <607> is withdrawn. At least a portion of the vapour stream $S_{CB}$ <607> is condensed in the condenser $K_{RRC}$ <608> and at least a portion thereof is applied in liquid form to the top of the reaction column $RR_C$ <600> as reflux. The vapour stream $S_{CB}$ <607> is withdrawn either in gaseous form upstream of the condenser $K_{RRC}$ <608> (marked by dashed line) and/or in liquid form downstream of the condenser $K_{RRC}$ <608> as stream <609>.

A side stream $S_{ZC}$ <610> is preferably withdrawn from the reaction column $RR_C$ <600>, wherein energy is transferred to said stream via an intermediate evaporator $V_{ZC}$ <611> and $S_{ZC}$ <610> may subsequently be recycled to $RR_C$ <600>.

As the sodium methoxide solution $S_{CE1}$ <602> it is preferable to utilize at least a portion of the bottoms streams $S_{AP*}$ <104> and $S_{BP*}$ <204> obtained in the reaction columns $RR_A$ <100> and $RR_B$ <200>.

The bottoms evaporator $V_{SC'}$ <606> is heated via a heat transfer medium $W_1$ <502>, in particular water, transported by a pump <501> which absorbs heat from $S_{OA12}$ <4032> in the intermediate cooler $WT_X$ <402> and releases it in the bottoms evaporator $V_{SC}$ <606>.

Alternatively, energy may also be appropriately transferred to the bottoms evaporator $V_{SC}$ <606> or the other bottoms evaporator $V_{SC}$ <605> from another stream selected from $S_{OA2}$ <404>, $S_{OA11}$ <4031> and $S_{OA1}$ <403> before separation into $S_{OA11}$ and $S_{OA12}$. Energy may likewise be transferred to the ethanol stream $S_{CE1}$ <603>, the sodium methoxide solution $S_{CE1}$ <602> or the side stream $S_{ZC}$ <610> from at least one of the streams $S_{OA1}$ <403>, $S_{OA11}$ <4031>, $S_{OA12}$ <4032>, $S_{OA2}$ <404>.

3.9 FIG. 9

Figure 9:
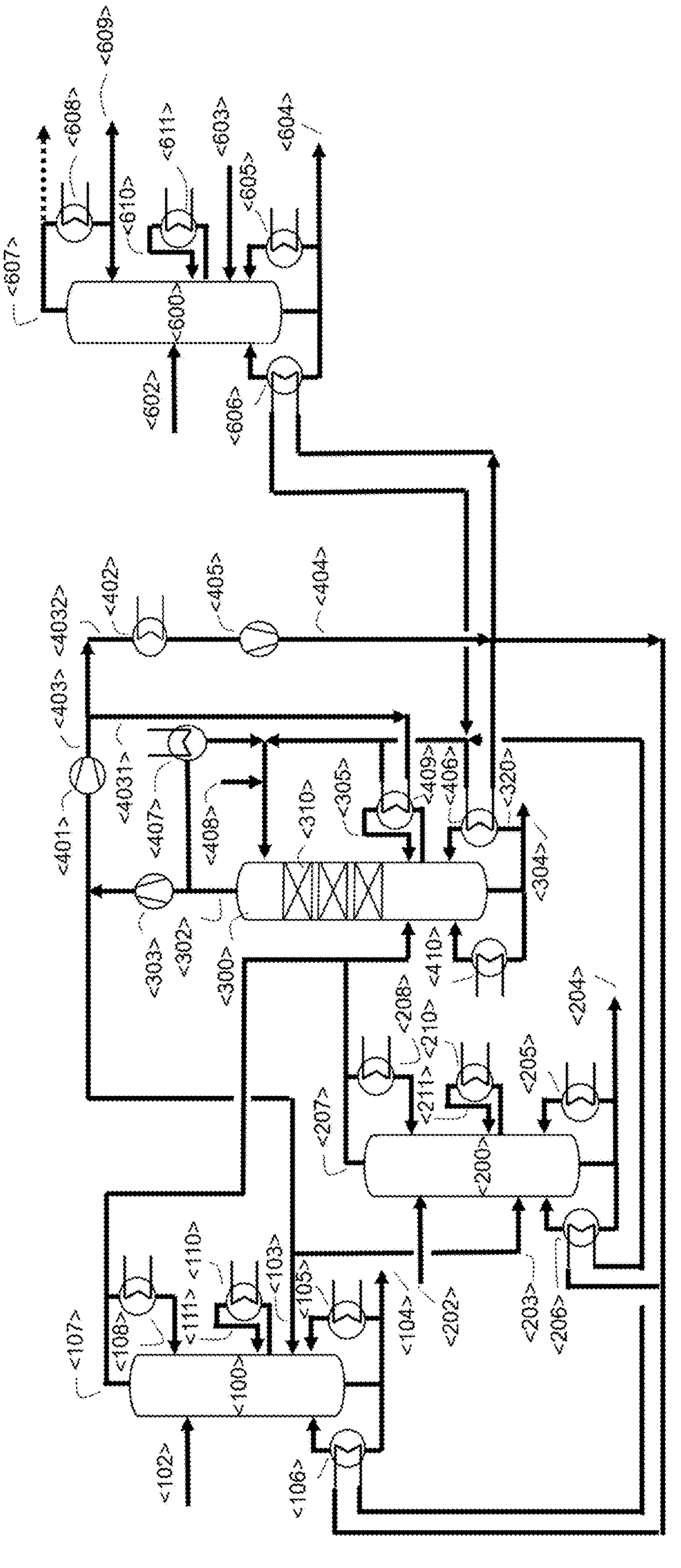

FIG. 9 shows an embodiment of the process according to the invention. This corresponds to the embodiment described in FIG. 8 with the difference that the heating of the bottoms evaporator $V_{SC}$ <606> is effected directly with a portion of $S_{OA}$2<404>.

3.10 FIG. 10

Figure 10:
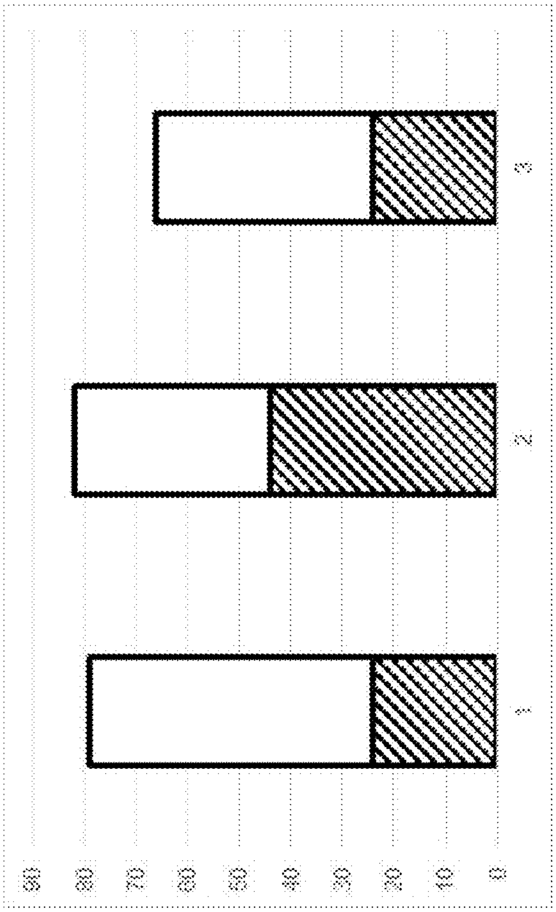

FIG. 10 illustrates the energy saving in the inventive process according to example 3 compared to the noninventive process according to examples 1 and 2. The x-axis describes the respective example and the y-axis the required power in kilowatts (heating steam and compressor power). The shaded portion of the bars shows the required heating power from low pressure steam while the white portion of the bars shows the sum of the compressor powers.

4. DETAILED DESCRIPTION OF THE INVENTION

The present invention relates to a process for producing at least one alkali metal alkoxide of formula $M_AOR$, wherein R is methyl, and wherein $M_A$ is a metal selected from sodium, potassium, preferably sodium.

The process according to the invention comprises with steps (a) to (f) a process for workup of a mixture G comprising water and alcohol ROH, wherein R is methyl. ROH is accordingly methanol.

4.1 Process for Workup of a Mixture G

The process according to the invention for workup of a mixture G comprises steps (a) to (f) of the process according to the invention for producing at least one alkali metal alkoxide of formula $M_AOR$.

The mixture G is especially gaseous, in which case it is also referred to as "vapours". The mixture G is the tops stream from a reaction column in which the alcohol ROH has been reacted with an alkali metal hydroxide NaOH or KOH to afford the corresponding alkali metal alkoxide NaOR or KOR.

According to the invention at least a portion of the vapor stream $S_{AB}$ and, if step (α2) is performed, at least a portion of the vapor stream $S_{BB}$ is employed as the mixture G employed in step (a).

The vapor stream $S_{AB}$ is obtained in step (α1) (described at point 4.2.1).

The vapor stream $S_{BB}$ is obtained in optional step (α2) if this step is performed (described at point 4.2.2).

The vapor stream $S_{BB}$ is only obtained if the optional step (α2) is performed. If the optional step (α2) is performed, $S_{BB}$ is obtained and at least a portion of $S_{BB}$ is employed as mixture G, the at least a portion of $S_{BB}$ is employed as mixture G in admixture with $S_{AB}$ or separately from $S_{AB}$.

In step (β) of the process at least a portion of the vapor stream $S_{AB}$ and, if step (α2) is performed, at least a portion of the vapor stream $S_{BB}$ is employed in admixture with $S_{AB}$ or separately from $S_{AB}$ as mixture G in step (a) of a process for workup of a mixture G comprising water and alcohol ROH.

According to the invention the mixture G comprising water and alcohol ROH is worked up with the process for workup of a mixture G.

4.1.1 Step (a) of the Process According to the Invention

In step (a) of the process according to the invention the mixture G is passed into a rectification column $RD_A$ and in $RD_A$ separated into at least one vapour stream $S_{OA}$ comprising ROH which is withdrawn at the upper end of $RD_A$ and at least one stream $S_{UA}$ comprising water which is withdrawn at the lower end of $RD_A$.

"At least one vapour stream $S_{OA}$ comprising ROH which is withdrawn at the upper end of $RD_A$" is to be understood as meaning that the vapour obtained at the upper end of $RD_A$ may be withdrawn there as one or more vapour streams. If said stream is withdrawn there in more than one vapour stream, the m vapour streams are referred to as "vapour stream $S_{OAI}$", "vapour stream $S_{OAII}$", [ . . . ], "vapour stream $S_{OAm}$", wherein "m" indicates the number of vapour streams withdrawn at the upper end of $RD_A$ (in Roman numerals).

"At least one vapour stream $S_{UA}$ comprising water which is withdrawn at the lower end of $RD_A$" is to be understood as meaning that water obtained at the lower end of $RD_A$ may be withdrawn there as one or more streams. If said stream is withdrawn there in more than one stream, the n streams are referred to as "stream $S_{UAI}$", "stream $S_{UAII}$", [ . . . ], "stream $S_{UAn}$", wherein "n" is the number of streams withdrawn at the lower end of $RD_A$ (in Roman numerals).

The mixture G may be introduced to the rectification column $RD_A$ via one or more feed points. It is introduced via two or more feed points for example in the embodiments in which step (α2) is performed in the process according to the preferred aspect of the invention and in step (β) at least a portion of the vapour stream $S_{BB}$ is employed separately from $S_{AB}$ as mixture G in step (a) of the process. In this embodiment the mixture G is thus introduced into the rectification column $RD_A$ as two separate streams.

In the embodiments of the present invention in which the mixture G is passed into the rectification column $RD_A$ as two or more separate streams it is advantageous when the feed points for the individual streams are at substantially the same height on the rectification column $RD_A$.

In a preferred embodiment of step (a) of the process according to the invention the mixture G is in a rectification column $RD_A$ separated into a vapour stream $S_{OA}$ comprising ROH which is withdrawn at the upper end of $RD_A$ and a stream $S_{UA}$ comprising water which is withdrawn at the lower end of $RD_A$.

Another term for "upper end of a rectification column" is "head".

Another term for "lower end of a rectification column" is "bottom" or "foot".

The pressure of the at least one vapour stream $S_{OA}$ is referred to as "$p_{OA}$" and its temperature as "$T_{OA}$". This relates especially to the pressure and temperature of the at least one vapour stream $S_{OA}$ when it is withdrawn from the rectification column $RD_A$ in step (a).

The pressure $p_{OA}$ is especially in the range from 0.5 bar abs. to 8 bar abs., more preferably in the range from 0.6 bar abs. to 7 bar abs., more preferably in the range from 0.7 bar abs. to 6 bar abs., yet more preferably in the range from 1 bar abs. to 5 bar abs., and is most preferably 1 bar abs. to 4 bar abs.

The temperature $T_{OA}$ is especially in the range from 45° C. to 150° C., more preferably in the range from 48° C. to 140° C., more preferably in the range from 50° C. to 130° C., yet more preferably in the range from 60° ° C. to 120° C., most preferably in the range from 60° C. to 110° C.

Any desired rectification column known to those skilled in the art may be employed as rectification column $RD_A$ in step (a) of the process. The rectification column $RD_A$ preferably contains internals. Suitable internals are, for example, trays, unstructured packings or structured packings. As trays, use is normally made of bubble cap trays, sieve trays, valve trays, tunnel trays or slit trays. Unstructured packings are generally beds of random packing elements. Packing elements normally used are Raschig rings, Pall rings, Berl saddles or Intalox® saddles. Structured packings are for example marketed under the trade name Mellapack® from Sulzer. Apart from the internals mentioned, further suitable internals are known to a person skilled in the art and can likewise be used.

Preferred internals have a low specific pressure drop per theoretical plate. Structured packings and random packing elements have, for example, a significantly lower pressure drop per theoretical plate than trays. This has the advantage that the pressure drop in the rectification column $RD_A$ remains as low as possible and the mechanical power of the compressor and the temperature of the alcohol/water mixture to be evaporated therefore remain low.

When the rectification column $RD_A$ contains structured packings or unstructured packings these may be divided or in the form of an uninterrupted packing. However, at least two packings are typically provided, one packing above the feed point for the mixture G and one packing below the feed point for the mixture G. It is also possible to provide one packing above the feed point for the mixture G and two or more trays below the feed point of the mixture G. If an unstructured packing is used, for example a random packing, the random packing elements are typically disposed on a suitable support grid (for example sieve tray or mesh tray).

In step (a) of the process according to the invention the at least one vapour stream $S_{OA}$ comprising ROH is then withdrawn at the upper end of the rectification column $RD_A$. The preferred mass fraction of ROH in this vapour stream $S_{OA}$ is ≥99% by weight, more preferably ≥99.6% by weight, yet more preferably ≥99.9% by weight, wherein the remainder is especially water.

Withdrawn at the lower end of $RD_A$ is at least one stream $S_{UA}$ comprising water which may preferably comprise <1% by weight, more preferably ≤5000 ppmw, yet more preferably ≤2000 ppmw of alcohol.

The withdrawal of the at least one vapour stream $S_{OA}$ comprising ROH at the top of the rectification column $RD_A$ is to be in particular understood as meaning in the context of the present invention that the at least one vapour stream $S_{OA}$ is withdrawn above the internals in the rectification column $RD_A$ as a top stream or as a side stream.

The withdrawal of the at least one stream $S_{UA}$ comprising water at the bottom of the rectification column $RD_A$ is to be in particular understood as meaning in the context of the present invention that the at least one stream $S_{UA}$ is withdrawn as a bottoms stream or at the lower tray of the rectification column $RD_A$.

The rectification column $RD_A$ is operated with or without, preferably with, reflux.

"With reflux" is to be understood as meaning that the vapour stream $S_{OA}$ withdrawn at the upper end of the rectification column $RD_A$ is not completely discharged but rather partially condensed and returned to the respective rectification column $RD_A$. In the cases where such a reflux is established the reflux ratio is preferably 0.0001 to 1, more preferably 0.0005 to 0.9, yet more preferably 0.001 to 0.8.

A reflux may be established such that a condenser $K_{RD}$ is attached at the top of the rectification column $RD_A$. In the condenser $K_{RD}$ the respective vapour stream $S_{OA}$ is partially condensed and returned to the rectification column $RD_A$. Generally and in the context of the present invention a reflux ratio is to be understood as meaning the ratio of the proportion of the mass flow withdrawn from the column (kg/h) that is recycled to the respective column in liquid form (reflux) to the proportion of this mass flow (kg/h) that is discharged from the respective column in liquid form or gaseous form.

4.1.2 Step (b) of the Process According to the Invention

In step (b) of the process according to the invention at least one side stream $S_{ZA}$ is withdrawn from $RD_A$ and recycled to $RD_A$.

In a preferred embodiment of step (b) of the process according to the invention a side stream $S_{ZA}$ is withdrawn from $RD_A$ and recycled to $RD_A$.

"Side stream $S_{ZA}$ from $RD_A$" is according to the invention to be understood as meaning that the stream is withdrawn at a withdrawal point $E_{ZA}$ below the head and above the bottom of $RD_A$ and in particular additionally recycled to $RD_A$ at a feed point $Z_{ZA}$ (this is the point at which the respective side stream $S_{ZA}$ is recycled to the respective rectification column $RD_A$) below the head and above the bottom of $RD_A$.

This is to be understood as meaning in particular that the withdrawal point $E_{ZA}$ and preferably also the feed point $Z_{ZA}$ of the respective side stream $S_{ZA}$ on the rectification column $RD_A$ is below the withdrawal points $E_{OA}$ for all vapour streams $S_{OA}$ withdrawn from $RD_A$, preferably at least 1, more preferably at least 5, yet more preferably at least 10, theoretical plates below the withdrawal point $E_{OA}$ for the vapour stream $S_{OA}$ withdrawn from $RD_A$ whose withdrawal point $E_{OA}$ is furthest down the rectification column $RD_A$.

This is also to be understood as meaning in particular that the withdrawal point $E_{ZA}$ and preferably also the feed point $Z_{ZA}$ of the respective side stream $S_{ZA}$ on the rectification column $RD_A$ is above the withdrawal points $E_{UA}$ for all streams $S_{UA}$ withdrawn from $RD_A$, preferably at least 1, more preferably at least 2, yet more preferably at least 4, theoretical plates above the withdrawal point $E_{UA}$ for the stream $S_{UA}$ whose withdrawal point $E_{UA}$ is furthest up the rectification column $RD_A$.

In the cases in which at least one vapour stream $S_{OA}$ is at least partially recycled into the rectification column $RD_A$ (which is the case when a reflux is established at the rectification column $RD_A$ for example) the feed point $Z_{OA}$ (i.e. the point at which the at least one vapour stream $S_{OA}$ is at least partially recycled into the rectification column $RD_A$)

of the at least one vapour stream $S_{OA}$ is especially also above the withdrawal points $E_{ZA}$ and especially also above the feed points $Z_{ZA}$ for all side streams $S_{ZA}$ withdrawn from $RD_A$, preferably at least 1, more preferably at least 5, yet more preferably at least 10, theoretical plates above the highest point of all withdrawal and feed points for all side streams $S_{ZA}$ withdrawn from $RD_A$.

In the cases in which at least one stream $S_{UA}$ is at least partially recycled into the rectification column $RD_A$ the feed point $Z_{UA}$ (i.e. the point at which the at least one stream $S_{UA}$ is at least partially recycled into the rectification column $RD_A$) of the at least one stream $S_{UA}$ is especially also below the withdrawal points $E_{ZA}$ and especially also below the feed points $Z_{ZA}$ for all side streams $S_{ZA}$ withdrawn from $RD_A$, preferably at least 1, more preferably at least 2, yet more preferably at least 4, theoretical plates below the lowest point of all withdrawal and feed points for all side streams $S_{ZA}$ withdrawn from $RD_A$.

The withdrawal point $E_{ZA}$ of the side stream $S_{ZA}$ and the feed point $Z_{ZA}$ of the side stream $S_{ZA}$ on the rectification column $RD_A$ may be positioned between the same trays of $RD_A$. However, they may also be at different heights.

In a preferred embodiment of the process according to the invention the withdrawal point $E_{ZA}$ and preferably also the feed point $Z_{ZA}$ of the at least one side stream $S_{ZA}$ on the rectification column $RD_A$ are below the feed point $Z_G$, by which the mixture G is passed into the rectification column $RD_A$, and above the bottom of $RD_A$. It is yet more preferable when the withdrawal point $E_{ZA}$ and preferably also the feed point $Z_{ZA}$ of the at least one side stream $S_{ZA}$ on the rectification column $RD_A$ are also below the rectification section of $RD_A$.

In a particularly preferred embodiment of the process according to the invention the withdrawal point $E_{ZA}$ and more preferably also the feed point $Z_{ZA}$ of the at least one side stream $S_{ZA}$ on the rectification column $RD_A$ are in the upper 4/5, preferably upper 3/4, preferably upper 7/10, more preferably upper 2/3, more preferably upper 1/2, of the region of the rectification column $RD_A$ below the feed point $Z_G$, by which the mixture G is passed into the rectification column $RD_A$, and above the uppermost of all withdrawal and feed points for all streams $S_{UA}$ withdrawn from $RD_A$. It is yet more preferable when the withdrawal point $E_{ZA}$ and preferably also the feed point $Z_{ZA}$ of the at least one side stream $S_{ZA}$ on the rectification column $RD_A$ are then also below the rectification section of $RD_A$.

In a further particularly preferred embodiment of the process according to the invention the rectification column $RD_A$ contains a rectification section and the withdrawal point $E_{ZA}$ and more preferably also the feed point $Z_{ZA}$ of the at least one side stream $S_{ZA}$ on the rectification column $RD_A$ are in the upper 4/5, preferably upper 3/4, preferably upper 7/10, more preferably upper 2/3, more preferably upper 1/2, of the region of the rectification column $RD_A$ below the rectification section and above the uppermost of all withdrawal and feed points for all streams $S_{UA}$ withdrawn from $RD_A$.

4.1.3 Step (c) of the Process According to the Invention

In step (c) of the process according to the invention at least a portion of the at least one vapour stream $S_{OA}$ ("at least a portion of the at least one vapour stream $S_{OA}$"="at least a portion of $S_{OA}$") is compressed. This affords a vapour stream $S_{OA1}$ which is compressed with respect to $S_{OA}$.

The pressure of the vapour stream $S_{OA1}$ is referred to as "$p_{OA1}$" and its temperature as "$T_{OA1}$".

The pressure $p_{OA1}$ is higher than $p_{OA}$. The precise value of $p_{OA1}$ may be adjusted by those skilled in the art according to the requirements in step (d) provided that the condition $p_{OA1}>p_{OA}$ is met. The quotient of $p_{OA1}/p_{OA}$ (pressures in bar abs. in each case) is preferably in the range from 1.1 to 10, more preferably 1.2 to 8, more preferably 1.25 to 7, most preferably 1.3 to 6.

The temperature $T_{OA1}$ is especially higher than the temperature $T_{OA}$ and the quotient of $T_{OA1}/T_{OA}$ (temperature in ° C. in each case) is preferably in the range from 1.03 to 10, more preferably 1.04 to 9, more preferably 1.05 to 8, more preferably 1.06 to 7, more preferably 1.07 to 6, most preferably 1.08 to 5.

The preferred values of $p_{OA1}$ and $T_{OA1}$ also apply with preference to $S_{OA11}$ and $S_{OA12}$.

The compressing of the at least a portion of the vapour stream $S_{OA}$ in step (c) may be carried out in any desired manner known to those skilled in the art. The compression may therefore be performed for example mechanically and as a single-stage or multi-stage compression, preferably a multi-stage compression. A multi-stage compression may employ a plurality of compressors of the same type or compressors of different types. A multi-stage compression may be carried out with one or more compressors. The use of single-stage compression or multi-stage compression depends on the compression ratio and thus on the pressure to which the vapour $S_{OA}$ is to be compressed.

Any desired compressor, preferably mechanical compressor, known to those skilled in the art and capable of compressing gas streams is suitable as a compressor in the process according to the invention, in particular for compressing the vapour streams $S_{OA}$ to $S_{OA1}$ or $S_{OA12}$ to $S_{OA2}$. Suitable compressors are for example single-stage or multi-stage turbines, piston compressors, screw compressors, centrifugal compressors or axial compressors.

In a multi-stage compression compressors suitable for the respective pressure stages to be overcome are employed.

4.1.4 Step (d) of the Process According to the Invention

In step (d) of the process according to the invention energy is transferred from a first portion $S_{OA11}$ of the compressed vapour stream $S_{OA1}$ to $S_{ZA}$ before $S_{ZA}$ is recycled to $RD_A$.

$S_{OA1}$ is especially in step (d) initially divided into at least two portions $S_{OA11}$ and $S_{OA12}$. The ratio of the mass flows (in kg/h) of $S_{OA11}$ to $S_{OA12}$ is preferably in the range from 1:99 to 99:1, more preferably in the range from 1:50 to 50:1, yet more preferably in the range from 1:20 to 30:1, yet more preferably in the range from 5:20 to 15:1.

In step (d) of the process according to the invention energy is transferred from the first portion $S_{OA11}$ to $S_{ZA}$. Step (d) reduces the energy of $S_{OA11}$ and the stream $S_{OA11}$ thus especially undergoes at least partial condensation.

According to the invention "transfer of energy" is especially to be understood as meaning "heating", i.e. transfer of energy in the form of heat.

"Transfer of energy from a first portion $S_{OA11}$ of the compressed vapour stream $S_{OA1}$ to $S_{ZA}$" also comprises the cases in which a portion of $S_{OA11}$ is separated and energy is transferred to $S_{ZA}$ only from this portion. This is the case for example in embodiments of the invention in which energy is additionally transferred from $S_{OA11}$ to the crude product $RP_A$ and if step (α2) is performed alternatively or in addition to the crude product $RP_B$ (described in section 4.2).

The transfer of energy from $S_{OA11}$ to $S_{ZA}$, preferably the heating of $S_{ZA}$ by $S_{OA11}$, is preferably effected directly or indirectly.

"Directly" is to be understood as meaning that $S_{OA11}$ is contacted with $S_{ZA}$ without mixing of the two streams, thus transferring energy, in particular heat, from $S_{OA11}$ to $S_{ZA}$.

This may be performed by passing $S_{OA11}$ and $S_{ZA}$ through an intermediate evaporator $V_{ZRD}$ on the rectification column $RD_A$ so that $S_{OA11}$ effects heating of $S_{ZA}$.

The employed heat exchangers, in particular the heat exchangers $WT_X$, $WT_Y$, $WT_Z$ mentioned hereinbelow, may be heat exchangers known to those skilled in the art, in particular evaporators. In step (d) of the process according to the invention the transfer of energy, preferably heat, from $S_{OA11}$ to $S_{ZA}$ is effected in particular in an intermediate evaporator $V_{ZRD}$.

"Indirectly" is especially to be understood as meaning that $S_{OA11}$ is contacted with a heat transfer medium $W_1$, preferably via at least one heat exchanger $WT_X$, wherein the heat transfer medium is not $S_{ZA}$, and $W_1$ is thus distinct from $S_{ZA}$, thus transferring energy, preferably heat, from $S_{OA11}$ to $W_1$ without the two streams mixing, and the heat is then transferred from $W_1$ to $S_{ZA}$ by contacting $W_1$ and $S_{ZA}$, wherein $S_{ZA}$ and $W_1$ do or do not mix, but preferably do not mix. If $W_1$ and $S_{ZA}$ do not mix, the transfer of energy, preferably heat, is effected in particular in a further heat exchanger $WT_Y$.

In a further embodiment of the process according to the invention in the case of indirect energy transfer from $S_{OA11}$ to $S_{ZA}$, in particular heating of $S_{ZA}$ by $S_{OA11}$, energy, preferably heat, may also be initially transferred from $S_{OA11}$ to $W_1$, preferably by contacting via at least one heat exchanger $WT_X$, and then transferred from $W_1$ to a further heat transfer medium $W_2$ distinct from $S_{ZA}$, preferably by contacting via at least one heat exchanger $WT_Y$. The last step then effects transfer of the heat from $W_2$ to $S_{ZA}$, wherein $S_{ZA}$ and $W_2$ do or do not mix, but preferably do not mix. If $W_2$ and $S_{ZA}$ do not mix, the transfer of energy, preferably heat, is effected in particular in a further heat exchanger $WT_Z$.

It will be appreciated that still further heat transfer media $W_3$, $W_4$, $W_5$ etc. may accordingly be employed in further embodiments of the present invention.

Utilizable heat transfer media $W_1$ and further heat transfer media $W_2$, $W_3$, $W_4$, $W_5$ include any heat transfer media known to those skilled in the art, preferably selected from the group consisting of water; alcohol-water solutions; salt-water solutions, also including ionic liquids such as for example LiBr solutions, dialkylimidazolium salts such as especially dialkylimidazolium dialkylphosphates; mineral oils, for example diesel oils; thermal oils such as for example silicone oils; biological oils such as for example limonene; aromatic hydrocarbons such as for example dibenzyltoluene. The most preferred heat transfer medium $W_1$ is water.

Salt-water solutions that may be used are also described for example in DE 10 2005 028 451 A1 and WO 2006/134015 A1.

After step (d) $S_{OA11}$ may then be returned to rectification column $RD_A$, optionally together with fresh alcohol and/or with the reflux for rectification column $RD_A$. In a preferred embodiment further energy is transferred from $S_{OA11}$, especially after the transfer of energy to $S_{ZA}$.

In a preferred embodiment of the process according to the invention once $S_{OA11}$ has transferred energy to $S_{ZA}$ according to step (d) energy, preferably heat, is transferred from $S_{OA11}$ to $S_{OA}$, in particular to the portion of $S_{OA}$ sent to a compression, preferably the compression in step (c), wherein this may be a precompression of $S_{OA}$ or the compression of $S_{OA}$ to $S_{OA1}$. This is preferably the first compression to which the stream $S_{OA}$ is subjected once it has left the column $RD_A$. This makes it possible to employ a portion of the residual energy/residual heat still stored by $S_{OA11}$ in the process, in this case for heating of $S_{OA}$ to be compressed. This evaporates any droplets present in $S_{OA}$ and thus prevents entry of droplets into the compressor.

Other, preferred additional sinks for the energy, preferably heat, in $S_{OA11}$ are described hereinbelow (see paragraph 4.3).

Step (d) of the process according to the invention reflects one aspect of the unexpected effect of the present invention. The excess energy obtained upon compression of the vapour stream $S_{OA}$ to afford the compressed vapour stream $S_{OA1}$ does not dissipate without being utilized but rather is employed in the rectification. This is effected such that $S_{OA}$ is initially compressed to afford $S_{OA1}$, thus allowing adjustment to a value optimal for energy transfer from $S_{OA11}$ to $S_{ZA}$, and then a portion $S_{OA12}$ that is distinct from $S_{OA11}$ may be further compressed to afford $S_{OA2}$. The heat of condensation obtained upon further compression of $S_{OA12}$ to afford $S_{OA2}$ is introduced into the column in the bottoms evaporator. The required additional compressor power is less than the heating steam power saved thereby. The process according to the invention requires less energy than those of the prior art, such as are shown in examples 1 and 2. The compression to afford $S_{OA2}$ allows the pressure and temperature of $S_{OA2}$ to be adjusted such that optimal energy transfer from $S_{OA2}$ to $S_{UA1}/S_{UA}$ may be effected.

4.1.5 Step (e) of the Process According to the Invention

In step (e) of the process of the invention a portion $S_{OA12}$ of the compressed vapour stream $S_{OA1}$ that is distinct from $S_{OA11}$ is subjected to further compression to afford a vapour stream $S_{OA2}$ that is compressed relative to $S_{OA11}$.

It will be appreciated that after performance of step (e) $S_{OA2}$ is also compressed relative to $S_{OA12}$ and $S_{OA1}$.

The pressure of the vapour stream $S_{OA2}$ is referred to as "$p_{OA2}$" and its temperature as "$T_{OA2}$".

The pressure $p_{OA2}$ is higher than $p_{OA}$ and the quotient of $p_{OA2}/p_{OA1}$ (pressures in bar abs. in each case) is preferably in the range from 1.1 to 10, more preferably 1.2 to 8, more preferably 1.25 to 7, most preferably 1.3 to 6.

The temperature $T_{OA2}$ is especially higher than the temperature $T_{OA1}$ and the quotient of $T_{OA2}/T_{OA1}$ (temperature in ° C. in each case) is preferably in the range from 1.03 to 10, more preferably 1.04 to 9, more preferably 1.05 to 8, more preferably 1.06 to 7, more preferably 1.07 to 6, most preferably 1.08 to 5.

The compressing of $S_{OA12}$ in step (e) may be performed by processes known to those skilled in the art. The compression may therefore be performed for example mechanically and as a single-stage or multi-stage compression, preferably a multi-stage compression. A multi-stage compression may employ a plurality of compressors of the same type or compressors of different types. The use of single-stage compression or multi-stage compression depends on the pressure to which the vapour $S_{OA12}$ is to be compressed. A precompression described for $S_{OA}$ in the context of step (c) may also be performed for the compression of $S_{OA12}$ to $S_{OA2}$ but compression in one stage, i.e. using a compressor $VD_X$, is especially sufficient in step (e).

4.1.6 Step (f) of the Process According to the Invention

In step (f) of the process according to the invention energy is transferred from at least a portion of $S_{OA2}$ to at least a portion $S_{UA1}$ of the at least one stream $S_{UA}$ before $S_{UA1}$ is recycled to $RD_A$.

In step (f) of the process energy is preferably transferred from at least a portion of $S_{OA2}$ to a portion $S_{UA1}$ of the at least one stream $S_{UA}$ before $S_{UA1}$ is recycled to $RD_A$.

Step (f) reduces the energy of $S_{OA2}$ and the stream $S_{OA2}$ thus especially undergoes at least partial condensation.

Step (f) of the process according to the invention comprises the following preferred embodiments (f1), (f2), (f3):

(f1) energy is transferred from at least a portion of $S_{OA2}$ to a portion $S_{UA1}$ of the at least one stream $S_{UA}$ and $S_{UA1}$ is then recycled to $RD_A$;

(f2) energy is transferred from at least a portion of $S_{OA2}$ to a portion $S_{UA1'}$ of the at least one stream $S_{UA}$ and a portion $S_{UA1}$ of $S_{UA1'}$ is then recycled to $RD_A$;

(f3) energy is transferred from at least a portion of $S_{OA2}$ to the whole of stream $S_{UA}$ and then the whole of stream $S_{UA}$ or only a portion $S_{UA1}$ of stream $S_{UA}$, preferably only a portion $S_{UA1}$ of stream $S_{UA}$, is recycled into $RD_A$.

The transfer of energy from at least a portion of $S_{OA2}$ to the at least a portion $S_{UA1}$ of the at least one stream $S_{UA}$, preferably the heating of the at least a portion $S_{UA1}$ of the at least one stream $S_{UA}$ by at least a portion of $S_{OA2}$, is preferably effected directly or indirectly.

"Directly" is to be understood as meaning that at least a portion of $S_{OA2}$ is contacted with the at least a portion $S_{UA1}$ of the at least one stream $S_{UA}$ without mixing of the two streams, thus transferring energy, in particular heat, from at least a portion of $S_{OA2}$ to the at least a portion $S_{UA1}$ of the at least one stream $S_{UA}$.

This may be performed by passing the at least a portion of $S_{OA2}$ and the at least a portion $S_{UA1}$ of the at least one stream $S_{UA}$ through an bottoms evaporator $V_{SRD}$ on the rectification column $RD_A$ so that $S_{OA11}$ effects heating of the at least a portion $S_{UA}$ of the at least one stream $S_{UA}$.

The employed heat exchangers, in particular the heat exchangers $WT_X$, $WT_Y$, $WT_Z$ mentioned hereinbelow, may be heat exchangers known to those skilled in the art, in particular evaporators. In step (f) of the process according to the invention the transfer of energy, preferably heat, from at least a portion of $S_{OA2}$ to the at least a portion $S_{UA1}$ of the at least one stream $S_{UA}$ is in particular effected in a bottoms evaporator $V_{SRD}$.

"Indirectly" is especially to be understood as meaning that the at least a portion of $S_{OA2}$ is contacted with at least one heat transfer medium $W_1$ preferably via at least one heat exchanger $WT_X$, wherein the heat transfer medium is not the at least a portion $S_{UA}$ of the at least one stream $S_{UA}$ and $W_1$ is thus distinct therefrom, thus transferring energy, preferably heat, from the at least a portion of $S_{OA2}$ to the at least one heat transfer medium $W_1$ without the two streams mixing, and the heat is then transferred from $W_1$ to the at least a portion $S_{UA}$ of the at least one stream $S_{UA}$ by contacting $W_1$ with the relevant component, wherein the at least a portion $S_{UA1}$ of the at least one stream $S_{UA}$ and $W_1$ do or do not mix, but preferably do not mix.

In a further embodiment of the process according to the invention in the case of indirect energy transfer from at least a portion of $S_{OA2}$ to the at least a portion $S_{UA1}$ of the at least one stream $S_{UA}$, in particular heating of the at least a portion $S_{UA1}$ of the at least one stream $S_{UA}$ by the at least a portion of $S_{OA2}$, energy, preferably heat, may also be initially transferred from $S_{OA2}$ to $W_1$, preferably by contacting via at least one heat exchanger $WT_X$, and then transferred from $W_1$ to a further heat transfer medium $W_2$ distinct from the at least a portion $S_{UA1}$ of the at least one stream $S_{UA}$, preferably by contacting via at least one heat exchanger $WT_Y$. The last step then effects transfer of the heat from $W_2$ to the at least a portion $S_{UA}$ of the at least one stream $S_{UA}$, wherein the at least a portion $S_{UA1}$ of the at least one stream $S_{UA}$ and $W_2$ do or do not mix, but preferably do not mix. It will be appreciated that still further heat transfer media $W_3$, $W_4$, $W_5$ etc. may accordingly be employed in further embodiments of the present invention.

Utilizable heat transfer media $W_1$ and further heat transfer media $W_2$, $W_3$, $W_4$, $W_5$ used include any heat transfer media known to those skilled in the art, preferably selected from the group consisting of water; alcohol-water solutions; salt-water solutions, also including ionic liquids such as for example LiBr solutions, dialkylimidazolium salts such as especially dialkylimidazolium dialkylphosphates; mineral oils, for example diesel oils; thermal oils such as for example silicone oils; biological oils such as for example limonene; aromatic hydrocarbons such as for example dibenzyltoluene. The most preferred heat transfer medium $W_1$ is water.

Salt-water solutions that may be used are also described for example in DE 10 2005 028 451 A1 and WO 2006/134015 A1.

After step (f) the at least a portion of $S_{OA2}$ may then be returned to the rectification column $RD_A$, optionally together with fresh alcohol and/or with the reflux for the rectification column $RD_A$ and/or with the stream $S_{OA11}$ obtained after performance of step (d). In a preferred embodiment further energy is transferred from at least a portion of $S_{OA2}$, especially after the transfer of energy to the at least a portion $S_{UA1}$ of $S_{UA}$.

In a preferred embodiment of the process according to the invention once energy has been transferred from the at least a portion of $S_{OA2}$ to the at least a portion $S_{UA1}$ of $S_{UA}$ according to step (f) energy, more preferably heat, is transferred from the at least a portion of $S_{OA2}$ to $S_{OA}$, in particular to the portion of $S_{OA}$ which is sent to a compression, preferably the compression in step (c), wherein this may be a precompression of $S_{OA}$ or the compression of $S_{OA}$ to afford $S_{OA1}$. This is preferably the first compression to which the stream $S_{OA}$ is subjected once it has left the column $RD_A$. This makes it possible to employ a portion of the residual energy/residual heat still stored by the at least a portion of $S_{OA2}$ in the process, in this case for heating of $S_{OA}$ to be compressed.

Other, preferred additional sinks for the energy, preferably heat, in the at least a portion of $S_{OA2}$ are described hereinbelow (see paragraph 4.3).

4.2 Process for Producing at Least One Alkali Metal Alkoxide

The mixture G employed in the process for workup of a mixture G according to the invention is a water/methanol mixture withdrawn from a reaction column for producing alkali metal alkoxides.

The present invention thus relates to a process for producing at least one alkali metal alkoxide of formula $M_AOR$, wherein R is methyl, and wherein $M_A$ is a metal selected from sodium, potassium, preferably sodium.

ROH is accordingly methanol.

4.2.1 Step (α1)

In step (α1) of the process according to the invention a reactant stream $S_{AE1}$ comprising ROH is reacted with a reactant stream $S_{AE2}$ comprising $M_AOH$ in countercurrent in a reactive rectification column $RR_A$ to afford a crude product $RP_A$ comprising $M_AOR$, water, ROH, $M_AOH$.

According to the invention, a "reactive rectification column" is a rectification column in which the reaction according to step (α1) or step (α2) of the process of the invention proceeds at least in some parts is defined. It may also be abbreviated to "reaction column".

In step (α1) a bottoms product stream $S_{AP}$ comprising ROH and $M_AOR$ is withdrawn at the lower end of $RR_A$. A vapour stream $S_{AB}$ comprising water and ROH is withdrawn at the upper end of $RR_A$.

$M_A$ is selected from sodium, potassium, preferably sodium.

The reactant stream $S_{AE1}$ comprises ROH. In a preferred embodiment the mass fraction of ROH in $S_{AE1}$ is ≥95% by weight, yet more preferably ≥99% by weight, wherein $S_{AE1}$ otherwise comprises especially water.

The alcohol ROH employed in step (α1) as reactant stream $S_{AE1}$ may also be commercially available alcohol having an alcohol mass fraction of more than 99.8% by weight and a mass fraction of water of up to 0.2% by weight.

The reactant stream $S_{AE1}$ is preferably introduced in vapour form.

The reactant stream $S_{AE2}$ comprises $M_AOH$. In a preferred embodiment $S_{AE2}$ comprises not only $M_AOH$ but also at least one further compound selected from water, ROH. It is yet more preferable when $S_{AE2}$ comprises water in addition to $M_AOH$, thus rendering $S_{AE2}$ an aqueous solution of $M_AOH$.

When the reactant stream $S_{AE2}$ comprises $M_AOH$ and water the mass fraction of $M_AOH$ based on the total weight of the aqueous solution forming $S_{AE2}$ is especially in the range from 10% to 75% by weight, preferably from 15% to 54% by weight, more preferably from 30% to 53% by weight and particularly preferably from 40% to 52% by weight.

When the reactant stream $S_{AE2}$ comprises $M_AOH$ and ROH the mass fraction of $M_AOH$ in ROH based on the total weight of the solution forming $S_{AE2}$ is especially in the range from 10% to 75% by weight, preferably from 15% to 54% by weight, more preferably from 30% to 53% by weight and particularly preferably from 40% to 52% by weight.

In the particular case in which the reactant stream $S_{AE2}$ comprises both water and ROH in addition to $M_AOH$ it is particularly preferable when the mass fraction of $M_AOH$ in ROH and water based on the total weight of the solution forming $S_{AE2}$ is especially in the range from 10% to 575% by weight, preferably from 15% to 54% by weight, more preferably from 30% to 53% by weight and particularly preferably from 40% to 52% by weight.

Step (α1) is performed in a reactive rectification column (or "reaction column") $RR_A$.

Step (α2), explained further hereinbelow, is performed in a reactive rectification column (or "reaction column") $RR_B$.

The reaction column $RR_A/RR_B$ preferably contains internals. Suitable internals are, for example, trays, structured packings or unstructured packings. When the reaction column $RR_A/RR_B$ contains trays, then bubble cap trays, valve trays, tunnel trays, Thormann trays, cross-slit bubble cap trays or sieve trays are suitable. When the reaction column $RR_A/RR_B$ contains trays it is preferable to choose trays where not more than 5% by weight, more preferably less than 1% by weight, of the liquid trickles through the respective trays. The constructional measures required to minimize trickle-through of the liquid are familiar to those skilled in the art. In the case of valve trays, particularly tightly closing valve designs are selected for example. Reducing the number of valves also makes it possible to increase the vapour velocity in the tray openings to twice the value typically established. When using sieve trays it is particularly advantageous to reduce the diameter of the tray openings while maintaining or even increasing the number of openings.

When using structured or unstructured packings, structured packings are preferred in terms of uniform distribution of the liquid.

For columns comprising unstructured packings, especially comprising random packings, and for columns comprising structured packings, the desired characteristics of the liquid distribution may be achieved when the liquid trickling density in the edge region of the column cross section adjacent to the column shell, corresponding to about 2% to 5% of the total column cross section, is reduced compared to the other cross-sectional regions by up to 100%, preferably by 5% to 15%. This can easily be achieved by, for example, targeted distributions of the drip points of the liquid distributors or the holes thereof.

The process according to the invention may be performed either continuously or discontinuously. It is preferably performed continuously.

"Reaction of a reactant stream $S_{AE1}$ comprising ROH with a reactant stream $S_{AE2}$ comprising $M_AOH$ in countercurrent" is according to the invention achieved, in particular, as a result of the feed point for at least a portion of the reactant stream $S_{AE1}$ comprising ROH in step (α1) being located on the reaction column $RR_A$ below the feed point of the reactant stream $S_{AE2}$ comprising $M_AOH$.

The reaction column $RR_A$ preferably comprises at least 2, in particular 15 to 40, theoretical trays between the feed point of the reactant stream $S_{AE1}$ and the feed point of the reactant stream $S_{AE2}$.

The reaction column $RR_A$ may be operated as a pure stripping column. In this case the reactant stream $S_{AE1}$ comprising ROH is introduced in vapour form in the lower region of the reaction column $RR_A$.

Step (α1) also encompasses the case where a portion of the reactant stream $S_{AE1}$ comprising ROH is added in vapour form below the feed point of the reactant stream $S_{AE2}$ comprising aqueous sodium hydroxide solution $M_AOH$ but nevertheless at the upper end or in the region of the upper end of the reaction column $RR_A$. This makes it possible to reduce the dimensions of the lower region of the reaction column $RR_A$. When a portion of the reactant stream $S_{AE1}$ comprising ROH, in particular methanol, is added especially in vapour form at the upper end or in the region of the upper end of the reaction column $RR_A$ only a fraction of 10% to 70% by weight, preferably of 30% to 50% by weight, (in each case based on the total amount of the alcohol ROH employed in step (α1)) is introduced at the lower end of the reaction column $RR_A$ and the remaining fraction is added in vapour form in a single stream or divided into a plurality of substreams, preferably 1 to 10 theoretical trays, particularly preferably 1 to 3 theoretical trays, below the feed point of the reactant stream $S_{AE2}$ comprising $M_AOH$.

In the reaction column $RR_A$, the reactant stream $S_{AE1}$ comprising ROH is then reacted with the reactant stream $S_{AE2}$ comprising $M_AOH$ according to the reaction <1> described hereinabove to afford $M_AOR$ and $H_2O$, where these products are present in admixture with the reactants ROH and $M_AOH$ since an equilibrium reaction is concerned. Accordingly, a crude product $RP_A$ which comprises ROH and $M_AOH$ in addition to the products $M_AOR$ and water is obtained in step (α1) in the reaction column $RR_A$.

The bottoms product stream $S_{AP}$ comprising ROH and $M_AOR$ is then obtained and withdrawn at the lower end of $RR_A$.

A water-containing alcohol stream, presently described as "vapour stream $S_{AB}$ comprising water and ROH", is withdrawn at the upper end of $RR_A$, preferably at the column top of $RR_A$.

This vapour stream $S_{AB}$ comprising water and ROH is employed in step (β) at least partially as mixture G in step (a) of the process according to the invention. A portion of the alcohol obtained in stream $S_{OA}$ in the distillation in step (a) may be supplied to the reaction column $RR_A$ as reactant stream $S_{AE1}$.

In a preferred embodiment of the process according to the invention a portion of $S_{OA}$ is employed as reactant stream $S_{AE1}$ in step (α1) and if step (α2) is performed alternatively or in addition as reactant stream $S_{BE1}$ in step (α2).

In a more preferred embodiment of the process according to the invention 5% to 95% by weight, preferably 10% to 90% by weight, more preferably 20% to 80% by weight, yet more preferably 30% to 70% by weight, of the vapour stream $S_{OA}$ is employed as reactant stream $S_{AE1}$ or if step (α2) is performed alternatively or in addition as reactant stream $S_{BE1}$ in step (α2).

In this preferred embodiment it is advantageous to compress the portion of the stream $S_{OA}$ employed as reactant stream $S_{AE1}$/as reactant stream $S_{BE1}$.

The amount of the alcohol ROH comprised by the reactant stream $S_{AE1}$ is preferably chosen such that said alcohol also serves as a solvent for the alkali metal alkoxide $M_AOR$ obtained in the bottoms product stream $S_{AP}$. The amount of the alcohol ROH in the reactant stream $S_{AE1}$ is preferably chosen to achieve in the bottom of the reaction column the desired concentration of the alkali metal alkoxide solution which is withdrawn as a bottoms product stream $S_{AP}$ comprising ROH and $M_AOR$.

In a preferred embodiment of the process according to the invention, and especially in the cases where $S_{AE2}$ contains water in addition to $M_AOH$, the ratio of the total weight (masses; units: kg) of alcohol employed in step (α1) as reactant stream $S_{AE1}$ ROH to the total weight (masses; unit: kg) of $M_AOH$ employed in step (α1) as reactant stream $S_{AE2}$ is 4:1 to 50:1, more preferably 8:1 to 48:1, yet more preferably 10:1 to 45:1, yet still more preferably 20:1 to 40:1.

The reaction column $RR_A$ is operated with or without, preferably with, reflux.

"With reflux" is to be understood as meaning that the vapour stream $S_{AB}$/$S_{BB}$ comprising water and ROH withdrawn at the upper end of the respective column, in step (α1) from the reaction column $RR_A$, in step (α2) from the reaction column $RR_B$, is not completely discharged. Thus in step (β) the respective vapour stream $S_{AB}$/$S_{BB}$ is then not entirely employed as mixture G but rather at least partially, preferably partially, returned to the respective column as reflux, in step (α1) to the reaction column $RR_A$, in step (α2) to the reaction column $RR_B$. In the cases where such a reflux is established the reflux ratio is preferably 0.01 to 1, more preferably 0.02 to 0.9, yet more preferably 0.03 to 0.34, particularly preferably 0.04 to 0.27 and very particularly preferably 0.05 to 0.24.

A reflux may be established by attaching a condenser at the top of the respective column. In step (α1) this is achieved in particular by attaching a condenser $K_{RRA}$ to the reaction column $RR_A$. In step (α2) this is achieved in particular by attaching a condenser $K_{RRB}$ to the reaction column $RR_B$.

In the respective condenser the respective vapour stream $S_{AB}$/$S_{BB}$ is at least partially condensed and returned to the respective column, in step (α1) to the reaction column $RR_A$/$RR_B$.

In the embodiment in which a reflux is established on the reaction column $RR_A$ the $M_AOH$ employed in step (α1) as reactant stream $S_{AE2}$ may also be at least partially mixed with the reflux stream and the resulting mixture thus supplied to step (α1).

Step (α1) is performed especially at a temperature in the range from 45° C. to 150° C., preferably 47° C. to 120° C., more preferably 60° ° C. to 110° C., and at a pressure of 0.5 bar abs. to 40 bar abs., preferably in the range from 0.7 bar abs. to 5 bar abs., more preferably in the range from 0.8 bar abs. to 4 bar abs., more preferably in the range from 0.9 bar abs. to 3.5 bar abs., more preferably at 1.0 bar abs. to 3 bar abs.

The reaction column $RR_A$ comprises in a preferred embodiment at least one evaporator which is especially selected from intermediate evaporators $V_{ZA}$ and bottoms evaporators $V_{SA}$. The reaction column $RR_A$ particularly preferably comprises at least one bottoms evaporator $V_{SA}$.

According to the invention "intermediate evaporators" $V_Z$ are to be understood as meaning evaporators arranged above the bottom of the respective column, in particular above the bottom of the reaction column $RR_A$/$RR_B$ (then referred to as "$V_{ZA}$"/"$V_{ZB}$") or above the bottom of the rectification column $RD_A$ (then referred to as "$V_{ZRD}$"). In the case of $RR_A$/$RR_B$ said evaporators especially evaporate crude product $RP_A$/$RP_B$ which is withdrawn from the column as side stream $S_{ZAA}$/$S_{ZBA}$.

According to the invention "bottoms evaporators" Vs are to be understood as meaning evaporators which heat the bottom of the respective column, in particular the bottom of the reaction column $RR_A$/$RR_B$ or $RR_C$ as used in the preferred embodiment and more particularly described hereinbelow (then referred to as "$V_{SA}$" or "$V_{SA}$"/"$V_{SB}$" or "$V_{SB}$."/"$V_{SC}$" or "$V_{SC}$.") or the bottom of the rectification column $RD_A$ (then referred to as "$V_{SRD}$" Or "$V_{SRD}$."). In the case of $RR_A$/$RR_B$ said evaporators especially evaporate at least a portion of the bottoms product stream $S_{AP}$/$S_{BP}$. In the case of $RR_C$ said evaporators especially evaporate bottoms product stream $S_{CP}$. In the case of $RD_A$ said evaporators especially evaporate bottoms product stream $S_{UA}$ or a portion of $S_{UA}$, $S_{UA1}$.

An evaporator is typically arranged outside the respective reaction column or rectification column. Since evaporators transfer energy, in particular heat, from one stream to another they are heat exchangers WT. The mixture to be evaporated is withdrawn via a takeoff from the column and supplied to the at least one evaporator. In the case of the reaction column $RR_A$/$RR_B$ intermediate evaporation of the crude product $RP_A$/$RP_B$ comprises withdrawal thereof and supply thereof to the at least one intermediate evaporator $V_{ZA}$/$V_{ZB}$.

In the case of the rectification column $RD_A$ intermediate evaporation comprises withdrawal of at least one side stream $S_{ZA}$ from $RD_A$ and supply thereof to the at least one intermediate evaporator $V_{ZRD}$.

In the case of the rectification column $RD_A$ bottoms evaporation comprises withdrawal of at least one stream $S_{UA}$ from $RD_A$ and supply of at least a portion, preferably a portion, thereof to the at least one bottoms evaporator $V_{SRD}$.

The evaporated mixture is recycled back into the respective column optionally with a residual proportion of liquid via at least one feed. When the evaporator is an intermediate evaporator, i.e. in particular an intermediate evaporator $V_{ZA}/V_{ZB}/V_{ZRD}$, the takeoff by means of which the respective mixture is withdrawn and supplied to the evaporator is a side stream takeoff and the feed by means of which the evaporated mixture is returned to the respective column is a side stream feed. When the evaporator is a bottoms evaporator, i.e. heats the column bottoms, i.e. is in particular a bottoms evaporator $V_{SA}/V_{SB}/V_{SRD}$, at least a portion of the bottoms takeoff stream, in particular $S_{AP}/S_{BP}$, is supplied to the bottoms evaporator, evaporated and recycled back into the respective column in the region of the column bottom. However it is alternatively also possible to configure suitable tubes, for example on a suitable tray when using an intermediate evaporator or in the bottom of the respective column, traversed by the heat transfer medium, for example the respective compressed vapour stream $S_{OA11}/S_{OA2}$ (if $Vs/V_Z$ are located at the rectification column $RD_A$), or a heating medium $W_1$ In this case, the evaporation occurs on the tray or in the bottom region of the column. However, it is preferable to arrange the evaporator outside the respective column.

Suitable evaporators employable as intermediate evaporators and bottoms evaporators include for example natural circulation evaporators, forced circulation evaporators, forced circulation evaporators with decompression, kettle evaporators, falling film evaporators or thin film evaporators. Heat exchangers for the evaporator typically employed in the case of natural circulation evaporators and forced circulation evaporators are shell and tube or plate apparatuses. When using a shell and tube exchanger the heat transfer medium, for example the compressed vapour stream $S_{OA11}/S_{OA2}$ in $V_{SRD}/V_{ZRD}$ at the rectification column $RD_A$/ the heating medium $W_1$, may either flow through the tubes with the mixture to be evaporated flowing around the tubes or else the heat transfer medium, for example the compressed vapour stream $S_{OA11}/S_{OA2}$ in $V_{SRD}/V_{ZRD}$ at the rectification column $RD_A$/the heating medium $W_1$, flows around the tubes with the mixture to be evaporated flowing through the tubes. In the case of a falling-film evaporator, the mixture to be evaporated is typically introduced as a thin film on the inside of a tube and the tube is heated externally. In contrast to a falling-film evaporator, a thin-film evaporator additionally comprises a rotor with wipers which distributes the liquid to be evaporated on the inner wall of the tube to form a thin film.

In addition to the recited evaporator types it is also possible to employ any desired further evaporator type known to those skilled in the art and suitable for use on a rectification column.

When the evaporator operated for example with the compressed vapour stream $S_{OA11}$/the heating medium $W_1$ as heating vapour is an intermediate evaporator it is preferable when the intermediate evaporator is arranged in the stripping portion of the rectification column $RD_A$ in the region between the feed point of the mixture G and above the column bottom or in the case of the reaction columns $RR_A/RR_B$ below the feed point of the reactant stream $S_{AE2}$/ $S_{BE2}$. This makes it possible to introduce a predominant proportion of the heat energy via the intermediate evaporator. It is thus possible for example to introduce more than 80% of the energy via the intermediate evaporator. According to the invention the intermediate evaporator is preferably arranged and/or configured such that it is used to introduce more than 10%, in particular more than 20%, of the total energy required for the distillation.

When using an intermediate evaporator it is especially advantageous when the intermediate evaporator is arranged such that the respective rectification column/reaction column has 1 to 50 theoretical trays below the intermediate evaporator and 1 to 200 theoretical trays above the intermediate evaporator. It is especially preferred when the rectification column/reaction column has 2 to 10 theoretical trays below the intermediate evaporator and 20 to 80 theoretical trays above the intermediate evaporator.

The side stream takeoff by means of which the mixture from the rectification column/reaction column is supplied to the intermediate evaporator $V_Z$ and the side stream feed by means of which the evaporated mixture from the intermediate evaporator $V_Z$ is returned to the respective rectification column/reaction column may be positioned between the same trays of the column. However, it is also possible for the side stream takeoff and side stream feed to be arranged at different heights.

Such an intermediate evaporator $V_{ZA}$ can convert liquid crude product $RP_A$ present in the reaction column $RR_A$ comprising $M_AOR$, water, ROH, $M_AOH$ into the gaseous state, thus improving the efficiency of the reaction according to step (α1) of the process according to the invention.

Such an intermediate evaporator $V_{ZB}$ can convert liquid crude product $RP_B$ present in the reaction column $RR_B$ comprising $M_BOR$, water, ROH, $M_BOH$ into the gaseous state, thus improving the efficiency of the reaction according to step (α2) of the process according to the invention.

By arranging one or more intermediate evaporators $V_{ZA}$/ $V_{ZB}$ in the upper region of the reaction column $RR_A$ the dimensions in the lower region of the reaction column $RR_A$ can be reduced. In the embodiment having at least one, preferably two or more, intermediate evaporators $V_{ZA}/V_{ZB}$ it is also possible to introduce substreams of the ROH in liquid form in the upper region of the reaction column $RR_A$.

In a further preferred embodiment energy, preferably heat, is transferred from at least a portion of a stream selected from $S_{OA1}$, $S_{OA2}$, in particular selected from $S_{OA11}$, $S_{OA12}$, $S_{OA2}$, preferably selected from $S_{OA11}$, $S_{OA2}$, to the crude product $RP_A$ and if step (α2) is performed alternatively or in addition to the crude product $RP_B$.

"Transfer of energy, preferably heat, from at least a portion of $S_{OA1}$ to the crude product $RP_A$ and if step (α2) is performed alternatively or in addition to the crude product $RP_B$" also comprises the transfer of energy, preferably heat, from at least one stream selected from $S_{OA11}$, $S_{OA12}$, or from the stream $S_{OA1}$ before separation thereof into $S_{OA11}$, $S_{OA12}$, to the crude product $RP_A$ and if step (α2) is performed alternatively or in addition to the crude product $RP_B$. It also comprises the transfer of energy from a portion of $S_{OA11}$, $S_{OA12}$ to the crude product $RP_A$ and if step (α2) is performed alternatively or in addition to the crude product $RP_B$.

To this end especially a portion of the relevant stream selected from $S_{OA1}$, $S_{OA2}$ or a heat transfer medium $W_1$, to which energy had previously been transferred from the relevant stream selected from $S_{OA1}$, $S_{OA2}$, is at least partially passed through an intermediate evaporator $V_{ZA}/V_{ZB}$ and the energy from the relevant stream selected from $S_{OA1}$, $S_{OA2}$/ $W_1$ transferred to the crude product stream withdrawn via the side stream takeoff on $RR_A/RR_B$, in particular by utilizing the relevant stream selected from $S_{OA1}$, $S_{OA2}/W_1$ for heating the evaporator $V_{ZA}/V_{ZB}$.

According to the invention bottoms evaporators are arranged at the bottom of the respective rectification column $RD_A$/reaction column $RR_A$/$RR_B$/$RR_C$ and are then referred to as "$V_{SRD}$" or "$V_{SRD'}$"/"$V_{SA}$" Or "$V_{SA'}$"/"$V_{SB}$" Or "$V_{SB'}$"/"$V_{SC}$" or "$V_{SC'}$". A bottoms product stream (in particular $S_{AP}$/$S_{BP}$) present in the respective column (in particular reaction column $RR_A$/$RR_B$) may be passed into such a bottoms evaporator and for example ROH at least partially removed therefrom. In the case of $S_{AP}$/$S_{BP}$ this may afford a bottoms product stream $S_{AP*}$ having an elevated mass fraction of $M_AOR$ compared to $S_{AP}$ or a bottoms product stream $S_{BP*}$ having an elevated mass fraction of $M_BOR$ compared to $S_{BP}$.

In step (α1) of the process according to the invention a bottoms product stream $S_{AP}$ comprising ROH and $M_AOR$ is withdrawn at the lower end of the reaction column $RR_A$.

It is preferable when the reaction column $RR_A$ comprises at least one bottoms evaporator $V_{SA}$ through which the bottoms product stream $S_{AP}$ is then partially passed to partially remove ROH, thus affording a bottoms product stream $S_{AP*}$ having an elevated mass fraction of $M_AOR$ compared to $S_{AP}$.

In another preferred embodiment transfer of energy, preferably heat, from at least a portion of a stream selected from $S_{OA1}$, $S_{OA2}$, in particular selected from $S_{OA11}$, $S_{OA2}$, to the crude product $RP_A$ and if step (α2) is performed alternatively or in addition to the crude product $RP_B$ is therefore undertaken as follows:

Especially a portion of the relevant stream selected from $S_{OA1}$, $S_{OA2}$ or a heat transfer medium $W_1$, to which energy had previously been transferred from the relevant stream selected from $S_{OA1}$, $S_{OA2}$, is then at least partially passed through a bottoms evaporator $V_{SA}$/$V_{SB}$ and the energy from the relevant stream selected from $S_{OA1}$, $S_{OA2}$/$W_1$ transferred to the bottoms product stream $S_{AP}$/$S_{BP}$, in particular by utilizing the relevant stream selected from $S_{OA1}$, $S_{OA2}$/$W_1$ for heating the evaporator $V_{SA}$/$V_{SB}$.

The mass fraction of $M_AOR$ in the bottoms product stream $S_{AP*}$ is in particular elevated compared to the mass fraction of $M_AOR$ in the bottoms product stream $S_{AP}$ by at least 0.5%, preferably by ≥1%, more preferably by ≥2%, yet more preferably by ≥5%.

It is preferable when $S_{AP}$ or, if at least one bottoms evaporator $V_{SA}$ is used through which the bottoms product stream $S_{AP}$ is at least partially passed to at least partially remove ROH, $S_{AP*}$ has a mass fraction of $M_AOR$ in ROH in the range from 1% to 50% by weight, preferably 5% to 35% by weight, more preferably 15% to 35% by weight, most preferably 20% to 35% by weight, in each case based on the total mass of $S_{AP}$.

The mass fraction of residual water in $S_{AP}$/$S_{AP*}$ is preferably <1% by weight, preferably <0.8% by weight, more preferably <0.5% by weight, based on the total mass of $S_{AP}$.

The mass fraction of reactant $M_AOH$ in $S_{AP}$/$S_{AP*}$ is preferably <1% by weight, preferably <0.8% by weight, more preferably <0.5% by weight, based on the total mass of $S_{AP}$.

4.2.2 Step (α2) (Optional)

Step (α2) is an optional embodiment of the process according to the invention. This is to be understood as meaning that in the context of the preferred embodiment of the process according to the invention step (α2) is or is not performed. In optional step (α2), simultaneously with and spatially separate from step (α1), a reactant stream $S_{BE1}$ comprising ROH is reacted with a reactant stream $S_{BE2}$ comprising $M_BOH$ in countercurrent in a reactive rectification column $RR_B$ to afford a crude product $RP_B$ comprising $M_BOR$, water, ROH, $M_BOH$.

In step (α2) of the process according to the invention a bottoms product stream $S_{BP}$ comprising ROH and $M_BOR$ is withdrawn at the lower end of $RR_B$. A vapour stream $S_{BB}$ comprising water and ROH is withdrawn at the upper end of $RR_B$.

$M_B$ is selected from sodium, potassium, preferably potassium.

The reactant stream $S_{BE1}$ comprises ROH. In a preferred embodiment the mass fraction of ROH in $S_{BE1}$ is ≥95% by weight, yet more preferably ≥99% by weight, wherein $S_{BE1}$ otherwise comprises especially water.

The alcohol ROH employed in step (α2) of the process according to the invention as reactant stream $S_{BE1}$ may also be commercially available alcohol having an alcohol mass fraction of more than 99.8% by weight and a mass fraction of water of up to 0.2% by weight.

The reactant stream $S_{BE1}$ is preferably introduced in vapour form.

The reactant stream $S_{BE2}$ comprises $M_BOH$. In a preferred embodiment $S_{BE2}$ comprises not only $M_BOH$ but also at least one further compound selected from water, ROH. It is yet more preferable when $S_{BE2}$ comprises water in addition to $M_BOH$, thus rendering $S_{BE2}$ an aqueous solution of $M_BOH$.

When the reactant stream $S_{BE2}$ comprises $M_BOH$ and water the mass fraction of $M_BOH$ based on the total weight of the aqueous solution forming $S_{BE2}$ is especially in the range from 10% to 75% by weight, preferably from 15% to 54% by weight, more preferably from 30% to 53% by weight and particularly preferably from 40% to 52% by weight.

When the reactant stream $S_{BE2}$ comprises $M_BOH$ and ROH the mass fraction of $M_BOH$ in ROH based on the total weight of the solution forming $S_{BE2}$ is especially in the range from 10% to 75% by weight, preferably from 15% to 54% by weight, more preferably from 30% to 53% by weight and particularly preferably from 40% to 52% by weight.

In the particular case in which the reactant stream $S_{BE2}$ comprises both water and ROH in addition to $M_BOH$ it is particularly preferable when the mass fraction of $M_BOH$ in ROH and water based on the total weight of the solution forming $S_{BE2}$ is especially in the range from 10% to 75% by weight, preferably from 15% to 54% by weight, more preferably from 30% to 53% by weight and particularly preferably from 40% to 52% by weight.

Step (α2) of the process according to the invention is performed in a reactive rectification column (or "reaction column") $RR_B$. Preferred embodiments of the reaction column $RR_B$ are described in section 4.2.1.

"Reaction of a reactant stream $S_{BE1}$ comprising ROH with a reactant stream $S_{BE2}$ comprising $M_BOH$ in countercurrent" is according to the invention achieved, in particular, as a result of the feed point for at least a portion of the reactant stream $S_{BE1}$ comprising ROH in step (α2) being located on the reaction column $RR_B$ below the feed point of the reactant stream $S_{BE2}$ comprising $M_BOH$.

The reaction column $RR_B$ preferably comprises at least 2, in particular 15 to 40, theoretical trays between the feed point of the reactant stream $S_{BE1}$ and the feed point of the reactant stream $S_{BE2}$.

The reaction column $RR_A$ may be operated as a pure stripping column. In this case the reactant stream $S_{BE1}$ comprising ROH is introduced in vapour form in the lower region of the reaction column $RR_B$. Step (α2) of the process according to the invention also encompasses the case where a portion of the reactant stream $S_{BE1}$ comprising ROH is added in vapour form below the feed point of the reactant stream $S_{BE2}$ comprising aqueous sodium hydroxide solution $M_BOH$ but nevertheless at the upper end or in the region of the upper end of the reaction column $RR_B$. This makes it possible to reduce the dimensions of the lower region of the reaction column $RR_B$. When a portion of the reactant stream $S_{BE1}$ comprising ROH, in particular methanol, is added especially in vapour form at the upper end or in the region of the upper end of the reaction column $RR_B$ only a fraction of 10% to 70% by weight, preferably of 30% to 50% by weight, (in each case based on the total amount of the alcohol ROH employed in step (α2)) is introduced at the lower end of the reaction column $RR_B$ and the remaining fraction is added in vapour form in a single stream or divided into a plurality of substreams preferably 1 to 10 theoretical trays, particularly preferably 1 to 3 theoretical trays, below the feed point of the reactant stream $S_{BE2}$ comprising $M_BOH$.

In the reaction column $RR_B$ the reactant stream $S_{BE1}$ comprising ROH is then reacted with the reactant stream $S_{BE2}$ comprising $M_BOH$ according to the reaction <1> described hereinabove to afford $M_BOR$ and $H_2O$, where these products are present in admixture with the reactants ROH and $M_BOH$ since an equilibrium reaction is concerned. Accordingly a crude product $RP_B$ which contains not only the products $M_BOR$ and water but also ROH and $M_B$ is obtained in the reaction column $RR_B$ in step (α2) of the process according to the invention.

The bottom product stream $S_{BP}$ comprising ROH and $M_BOR$ is obtained and withdrawn at the lower end of $RR_B$.

A water-containing alcohol stream, presently described as "vapour stream $S_{BB}$ comprising water and ROH", is withdrawn at the upper end of $RR_B$, preferably at the column top of $RR_B$.

In step (β) of the process according to the invention at least a portion of this vapour stream $S_{BB}$ comprising water and ROH is employed especially as mixture G in step (a) of the process according to the invention. Said mixture is supplied to the rectification column $RD_A$ as mixture G in admixture with $S_{AB}$ or not, i.e. separate from $S_{AB}$. It is preferable when the vapour streams $S_{BB}$ and $S_{AB}$ are mixed and then the mixture is employed as mixture G in step (a) of the process according to the invention.

The amount of alcohol ROH present in the reactant stream $S_{BE1}$ is preferably selected so that it simultaneously serves as solvent for the alkali metal alkoxide $M_BOR$ present in the bottom product stream $S_{BP}$. The amount of the alcohol ROH in the reactant stream $S_{BE1}$ is preferably chosen to achieve in the bottom of the reaction column the desired concentration of the alkali metal alkoxide solution which is withdrawn as a bottoms product stream $S_{BP}$ comprising ROH and $M_BOR$.

In a preferred embodiment of the process according to the invention, and especially in the cases where $S_{BE2}$ contains water in addition to $M_BOH$, the ratio of the total weight (masses; units: kg) of alcohol employed in step (α2) as reactant stream $S_{BE1}$ ROH to the total weight (masses; unit: kg) of $M_BOH$ employed in step (α2) as reactant stream $S_{BE2}$ is 4:1 to 50:1, more preferably 8:1 to 48:1, yet more preferably 10:1 to 45:1, yet still more preferably 20:1 to 40:1.

The reaction column $RR_B$ is operated with or without, preferably with, reflux.

"With reflux" is to be understood as meaning that the vapour stream $S_{BB}$ withdrawn at the upper end of the respective column, the reaction column $RR_B$ in step (α2), comprising water and ROH is not completely discharged, i.e. in step (β) of the process according to the invention not completely employed as mixture G in step (a), i.e. supplied to the rectification column $RD_A$, but rather at least partially, preferably partially, returned to the respective column, the reaction column $RR_B$ in step (α2), as reflux. In the cases where such a reflux is established the reflux ratio is preferably 0.01 to 0.99, more preferably 0.02 to 0.9, yet more preferably 0.03 to 0.34, particularly preferably 0.04 to 0.27 and very particularly preferably 0.05 to 0.24.

In the embodiment in which a reflux is established for the reaction column $RR_B$ the $M_BOH$ employed in step (α2) as reactant stream $S_{BE2}$ may also be at least partially mixed with the reflux stream and the resulting mixture thus supplied to step (α2).

Optional step (α2) is performed especially at a temperature in the range from 45° C. to 150° C., preferably 47° C. to 120° C., more preferably 60° ° C. to 110° C., and at a pressure of 0.5 bar abs. to 40 bar abs. preferably in the range from 0.7 bar abs. to 5 bar abs., more preferably in the range from 0.8 bar abs. to 4 bar abs., more preferably in the range from 0.9 bar abs. to 3.5 bar abs., yet more preferably at 1.0 bar abs. to 3 bar abs.

The reaction column $RR_B$ comprises in a preferred embodiment at least one evaporator which is in particular selected from intermediate evaporators $V_{ZB}$ and bottoms evaporators $V_{SB}$. The reaction column $RR_B$ particularly preferably comprises at least one bottoms evaporator $V_{SB}$.

Such an intermediate evaporator $V_{ZB}$ can convert liquid crude product $RP_B$ present in the reaction column $RR_B$ comprising $M_BOR$, water, ROH, $M_BOH$ into the gaseous state, thus improving the efficiency of the reaction according to step (α2) of the process according to the invention.

By arranging one or more intermediate evaporators $V_{ZB}$ in the upper region of the reaction column $RR_B$ the dimensions in the lower region of the reaction column $RR_B$ can be reduced. In the embodiment having at least one, preferably two or more, intermediate evaporators $V_{ZB}$ it is also possible to introduce substreams of the ROH in liquid form in the upper region of the reaction column $RR_B$.

In step (α2) of the process according to the invention a bottoms product stream $S_{BP}$ comprising ROH and $M_BOR$ is withdrawn at the lower end of the reaction column $RR_B$.

It is preferable when the reaction column $RR_B$ comprises at least one bottoms evaporator $V_{SB}$ through which the bottoms product stream $S_{BP}$ is then at least partially passed to at least partially remove ROH, thus affording a bottoms product stream $S_{BP*}$ having an elevated mass fraction of $M_BOR$ compared to $S_{BP}$.

The mass fraction of $M_BOR$ in the bottoms product stream $S_{BP*}$ is in particular elevated compared to the mass fraction of $M_BOR$ in the bottoms product stream $S_{BP}$ by at least 0.5%, preferably by ≥1%, more preferably by ≥2%, yet more preferably by ≥5%.

It is preferable when $S_{BP}$ or, if at least one bottoms evaporator $V_{SB}$ is employed through which the bottoms product stream $S_{BP}$ is at least partially passed to at least partially remove ROH, $S_{BP*}$ has a mass fraction of $M_BOR$ in ROH in the range from 1% to 50% by weight, preferably 5% to 35% by weight, more preferably 15% to 35% by weight, most preferably 20% to 35% by weight, in each case based on the total mass of $S_{BP}$.

The mass fraction of residual water in $S_{BP}$/$S_{BP*}$ is preferably <1% by weight, preferably <0.8% by weight, more preferably <0.5% by weight, based on the total mass of $S_{BP}$.

The mass fraction of reactant $M_BOH$ in $S_{BP}/S_{BP*}$ is preferably <1% by weight, preferably <0.8% by weight, more preferably <0.5% by weight, based on the total mass of $S_{BP}$.

In the embodiments of the present process in which step (α2) is also performed it is preferable when the bottoms product stream $S_{AP}$ is at least partially passed through a bottoms evaporator $V_{SA}$ and ROH is at least partially removed from $S_{AP}$ to afford a bottoms product stream $S_{AP*}$ having an elevated mass fraction of $M_AOR$ compared to $S_{AP}$ and/or, preferably and, the bottoms product stream $S_{BP}$ is at least partially passed through a bottoms evaporator $V_{SB}$ and ROH is at least partially removed from $S_{BP}$ to afford a bottoms product stream $S_{BP*}$ having an elevated mass fraction of $M_BOR$ compared to $S_{BP}$.

In the embodiments of the present invention in which it is performed step (α2) of the process according to the invention is performed simultaneously with and spatially separate from step (α1). Spatial separation is ensured by performing steps (α1) and (α2) in the two reaction columns $RR_A$ and $RR_B$.

In an advantageous embodiment of the invention the reaction columns $RR_A$ and $RR_B$ are accommodated in one column shell, where the column is at least partially subdivided by at least one dividing wall. Such a column having at least one dividing wall will be referred to as "TRD". Such dividing wall columns are familiar to those skilled in the art and are described for example in U.S. Pat. No. 2,295,256, EP 0 122 367 A2, EP 0 126 288 A2, WO 2010/097318 A1 and by I. Dejanović, Lj. Matijašević, Ž. Olujić, Chemical Engineering and Processing 2010, 49, 559-580. CN 105218315 A likewise describes dividing wall columns which are used in the rectification of methanol.

In the dividing wall columns suitable for the process according to the invention the dividing walls preferably extend to the column floor and, in particular, preferably span at least a quarter, more preferably at least a third, yet more preferably at least half, yet more preferably at least two thirds, yet still more preferably at least three quarters, of the column by height. They divide the columns into at least two reaction spaces in which spatially separate reactions may be carried out. The reaction spaces provided by the at least one dividing wall may be of identical or different sizes.

In this embodiment the bottoms product streams $S_{AP}$ and $S_{BP}$ may be separately withdrawn in the respective regions separated by the dividing wall and preferably passed through the bottoms evaporator $V_{SA}/V_{SB}$ attached for each reaction space formed by the at least one reaction wall in which ROH is at least partially removed from $S_{AP}/S_{BP}$ to afford $S_{AP*}/S_{BP*}$.

In a preferred embodiment of the process according to the invention accordingly at least two, more preferably precisely two, of the columns selected from rectification column $RD_A$, reaction column $RR_A$ and if step (α2) is performed the reaction column $RR_B$ are accommodated in one column shell, wherein the columns are at least partially separated from one another by a dividing wall extending to the bottom of the column.

In the integrated system comprising reaction column $RR_A$ (or in the embodiments in which step (α2) is performed reaction column $RR_A$ and reaction column $RR_B$) and rectification column $RD_A$ in the process according to the invention the rectification column $RD_A$ is preferably operated at a pressure selected such that the pressure gradient between the columns is low.

The alcohol ROH is consumed in the process according to the invention and especially in a continuous process mode therefore requires replacement with fresh alcohol ROH.

Supply of the fresh alcohol ROH is thus especially carried out directly as reactant stream $S_{AE1}$ comprising ROH into the reaction column $RR_A$ or in the embodiments in which step (α2) is performed into the reaction columns $RR_A$ and $RR_B$.

In the process according to the invention it is further preferable to employ the ROH-comprising vapour stream $S_{OA}$ partially as reactant stream $S_{AE1}$ in step (α1) and optionally as reactant stream $S_{BE1}$ in step (α2). The compressed vapour stream $S_{OA1}$ may alternatively or in addition be employed partially as reactant stream $S_{AE1}$ in step (α1) and optionally as reactant stream $S_{BE1}$ in step (α2). In this preferred embodiment it is yet more preferable when the fresh alcohol ROH is added to the rectification column $RD_A$.

When the fresh alcohol ROH is added to the rectification column $RD_A$ it is preferably supplied either in the rectifying section of the rectification column $RD_A$ or directly at the top of the rectification column $RD_A$. The optimal feed point depends on the water content of the employed fresh alcohol and also on the desired residual water content in the vapour stream $S_{OA}$. The higher the proportion of water in the employed alcohol and the higher the purity requirements of the vapour stream $S_{OA}$ the more advantageous is a feed a number of theoretical plates below the top of the rectification column $RD_A$. Up to 20 theoretical plates below the top of the rectification column $RD_A$ and in particular 1 to 5 theoretical plates are preferred.

When the fresh alcohol ROH is added to the rectification column $RD_A$ it is added at the top of the rectification column $RD_A$ at temperatures up to boiling point, preferably at room temperature. A dedicated feed may be provided for the fresh alcohol or else when a portion of the alcohol withdrawn at the top of the rectification column $RD_A$ is recycled may be mixed therewith after condensation and supplied to the rectification column $RD_A$ together. In this case it is particularly preferable when the fresh alcohol is added to a condensate container in which the alcohol condensed from the vapour stream $S_{OA}$ is collected.

As described hereinabove, in an advantageous embodiment of the invention at least two of the columns selected from rectification column $RD_A$, reaction column $RR_A$ and if step (α2) is performed the reaction column $RR_B$ are accommodated in one column shell, wherein the columns are in each case at least partially separated from one another by a dividing wall extending to the bottom of the column. In the abovedescribed preferred embodiment in which step (α2) is performed these are thus separated from one another by two dividing walls, wherein the two dividing walls extend to the bottom of the column.

In this preferred embodiment the reaction to afford the crude product $RP_A$ according to step (α1) or the crude products $RP_A$ and $RP_B$ according to steps (α1) and (α2) are in particular performed in one part of the TRD, wherein the reactant stream $S_{AE2}$ and optionally the reactant stream $S_{BE2}$ are added below but at approximately the height of the upper end of the dividing wall and the reactant stream $S_{AE1}$ and optionally the reactant stream $S_{BE1}$ are added in vapour form at the lower end. The alcohol/water mixture formed above the feed point of the reactant stream then becomes distributed above the dividing wall over the entire column region which serves as rectifying section of the rectification column $RD_A$. The second/third lower part of the column which has been separated off by the dividing wall is the stripping section of the rectification column $RD_A$. The energy required for the distillation is then supplied via an evaporator at the lower end of the second portion of the column separated by the dividing wall, wherein this evaporator may be conventionally heated or heated with a portion of the compressed vapour stream $S_{OA2}$. When the evaporator is conventionally heated an intermediate evaporator heated with a portion of the compressed vapour stream $S_{OA11}$ may additionally be provided.

In the embodiments in which a portion of $S_{OA}$ is employed as reactant stream $S_{AE1}$ and/or reactant stream $S_{BE1}$ $S_{OA}$ is especially compressed with a first compressor $VD_{AB2}$ ("precompressed"), wherein the difference in the pressures inside the reaction columns $RR_A$ and $RR_B$ compared to the pressure in $RD_A$ may be taken into account.

Instead of the compressor $VD_{AB2}$ which is arranged downstream of the rectification column $RD_A$ and in which $S_{OA}$ is precompressed this preferred embodiment may also employ, alternatively or in addition, a compressor $VD_{AB1}$ which is arranged upstream of the rectification column $RD_A$ and through which the mixture G is passed before it is passed into $RD_A$.

Provided it is not recycled to $RD_A$ as reflux the remaining portion of the at least one vapour stream $S_{OA}$, i.e. especially the portion not employed as reactant stream $S_{AE1}$ and/or reactant stream $S_{BE1}$, is in this preferred embodiment then further compressed to afford $S_{OA1}$. According to the invention $S_{OA}$ becomes $S_{OA1}$ only in the compressor stage after which $S_{OA1}$ is divided into $S_{OA11}$ and $S_{OA12}$ as are employed in step (d) according to the invention. This compression to compress $S_{OA}$ into $S_{OA1}$ is in the figures and examples performed with the compressor $V_{D1}$ (referred to in the figures as <401>).

4.2.3 Step (β)

In step (B) of the process according to the invention at least a portion of the vapour stream $S_{AB}$, and if step (α2) is performed at least a portion of the vapour stream $S_{BB}$, in admixture with $S_{AB}$ Or separate from $S_{AB}$, is employed as mixture G in step (a) of the process according to the invention. If step (α2) is performed it is preferable when the at least a portion of the vapour stream $S_{AB}$ and the at least a portion of the vapour stream $S_{BB}$ are mixed and then employed as mixture G in step (a) of the process according to the invention.

"Employed as mixture G in step (a) of the process according to the invention" is in particular to be understood as meaning that the two streams $S_{AB}$ and $S_{BB}$ are passed into the rectification column $RD_A$ and are preferably previously mixed.

However, they may alternatively also be passed into the rectification column $RD_A$ at two different feed points.

4.3 Preferred Aspect: Process for Transalcoholization of an Alkali Metal Alkoxide In an advantageous embodiment of the present invention the energy comprised in at least one of the streams $S_{OA1}$, $S_{OA2}$, $S_{OA11}$, $S_{OA12}$ is used for operation of other industrial processes. This is advantageous especially in sites hosting integrated systems (chemistry parks, technology parks) where there is always a need for heat for heating. Especially in the case of integrated systems comprising two or more plants for alkali metal alkoxide production this energy may be advantageously utilized. Such integrated systems typically also comprise processes for transalcoholization as described in DE 27 26 491 A1. U.S. Pat. No. 3,418,383 A describes processes for transalcoholization from methoxides to propoxides.

A preferred aspect of the present invention provides that in the process according to the present invention in a reactive rectification column $RR_C$ a reactant stream $S_{CE1}$ comprising $M_cOR'$ and optionally R'OH is reacted in countercurrent with a reactant stream $S_{CE2}$ comprising R"OH to afford a crude product $RP_C$ comprising $M_cOR"$ and R'OH, wherein a bottoms product stream $S_{CP}$ comprising $M_cOR"$ is withdrawn at the lower end of $RR_C$ and a vapour stream $S_{CB}$ comprising R'OH is withdrawn at the upper end of $RR_C$, and wherein R' and R" are two distinct $C_1$ to $C_6$ hydrocarbon radicals and $M_C$ is a metal selected from sodium, potassium, preferably sodium, and wherein energy is transferred from at least a portion of a stream selected from $S_{OA1}$, $S_{OA2}$ to the crude product $RR_C$.

The process according to the invention according to the preferred aspect of the invention is a process for transalcoholization of a particular alkali metal alkoxide $M_cOR'$ to afford another alkali metal alkoxide $M_cOR"$ as described for example in DE 27 26 491 A1.

R' and R" are two distinct $C_1$ to $C_6$ hydrocarbon radicals, preferably two distinct $C_1$ to $C_4$ hydrocarbon radicals.

More preferably R' is methyl and R" is a $C_2$ to $C_4$ hydrocarbon radical, yet more preferably R'=methyl and R"=ethyl.

The process according to the preferred aspect of the invention (hereinbelow also referred to as "transalcoholization") is performed in a reactive rectification column $RR_C$. Suitable reactive rectification columns include columns described for $RR_A$ at point 4.2.1 in the context of step (α1).

The reaction column $RR_C$ is operated with or without, preferably with, reflux. If a reflux is established in particular the vapour $S_{CB}$ is partially or completely passed through a condenser $K_{RRC}$ and the condensed vapour may then be returned to the reaction column $RR_C$ or employed as reactant stream $S_{AE1}$ Or $S_{BE1}$. It may also be employed as the fresh alcohol stream in $RD_A$.

In the transalcoholization a bottoms product stream $S_{CP}$ comprising $M_cOR"$ is withdrawn at the lower end of $RR_C$. A vapour stream $S_{CB}$ comprising R'OH is withdrawn at the upper end of $RR_C$.

Preferably, in the embodiments of the transalcoholization which also comprise performing the process for producing an alkali metal alkoxide according to the invention the employed reactant stream $S_{CE1}$ comprising $M_cOR'$ and optionally R'OH preferably comprises at least a portion of $S_{AP}$, in particular since R=methyl and thus also R'=methyl. It is then particularly preferable when R"=ethyl. A transalcoholization of alkali metal methoxide to the corresponding alkali metal ethoxide is accordingly carried out.

In a preferred alternative in the embodiments of the transalcoholization which also comprise performing the process for producing an alkali metal alkoxide including step (α2) according to the invention the employed reactant stream $S_{CE1}$ comprising $M_cOR'$ and optionally R'OH preferably comprises at least a portion of $S_{BP}$, in particular since R=methyl and thus also R'=methyl. It is then particularly preferable when R"=ethyl. A transalcoholization of alkali metal methoxide to the corresponding alkali metal ethoxide is accordingly carried out.

When $S_{BP}$ and $S_{AP}$ comprise the same alkali metal alkoxide and the same alcohol ROH these two streams may also be employed separately or in admixture as $S_{CE1}$, i.e. in particular first mixed and then supplied to the column $RR_C$ as reactant stream $S_{CE1}$ or supplied to the column $RR_C$ separately as two reactant streams $S_{CE1}$.

The reactant stream $S_{CE2}$ comprises R"OH. In a preferred embodiment the mass fraction of R"OH in $S_{CE2}$ is ≥85% by weight, more preferably ≥90% by weight, wherein $S_{CE2}$ otherwise comprises in particular $M_cOR"$ or another denaturant. The alcohol R"OH employed as reactant stream $S_{CE2}$ may also be commercially available alcohol having an alcohol mass fraction of more than 99.8% by weight and a mass fraction of water of up to 0.2% by weight.

"Reaction of a reactant stream $S_{CE1}$ comprising $M_cOR'$ and optionally R'OH with a reactant stream $S_{CE2}$ comprising R"OH in countercurrent" is according to the invention ensured, in particular, as a result of the feed point for at least a portion of the reactant stream $S_{CE1}$ comprising $M_cOR'$ being located on the reaction column $RR_C$ above the feed point of the reactant stream $S_{CE2}$ comprising R"OH.

The reaction column $RR_C$ is operated with or without, preferably with, reflux.

In a preferred embodiment the reaction column $RR_C$ comprises at least one evaporator which is in particular selected from intermediate evaporators $V_{ZC}$ and bottoms evaporators $V_{SC}$. The reaction column $RR_C$ particularly preferably comprises at least one bottoms evaporator $V_{SC}$.

In the case of the reaction column $RR_C$ intermediate evaporation comprises withdrawal of at least one side stream $S_{ZC}$ from $RR_C$ and supply thereof to the at least one intermediate evaporator $V_{ZC}$.

In the case of the reaction column $RR_C$ bottoms evaporation comprises withdrawal of at least one stream, for example $S_{CP}$ from $RR_C$ and supply of at least a portion, in the case of $S_{CP}$ preferably a portion, to the at least one bottoms evaporator $V_{SC}$.

Suitable evaporators employable as intermediate evaporators and bottoms evaporators are described in section 4.2.1.

In the transalcoholization, energy, preferably heat, is transferred from at least a portion of a stream selected from $S_{OA1}$, $S_{OA2}$ to the crude product $RP_C$. This is preferably effected by transfer of energy from at least a portion of a stream selected from $S_{OA1}$, $S_{OA2}$ to $S_{CE1}$ or $S_{CE2}$ before passage thereof into $RR_C$ followed by transfer of energy from $S_{CE1}/S_{CE2}$ to the crude product $RP_C$ present in $RR_C$, with which they mix together.

Accordingly energy, preferably heat, from at least a portion of a stream selected from $S_{OA1}$, $S_{OA2}$, in particular from at least one stream selected from $S_{OA11}$, $S_{OA12}$, $S_{OA2}$, preferably from at least one stream selected from $S_{OA11}$, a portion of $S_{OA2}$, is transferred to the crude product $RP_C$.

"Transfer of energy, preferably heat, from at least a portion of $S_{OA1}$ to the crude product $RP_C$" also comprises the transfer of energy, preferably heat, from at least one stream selected from $S_{OA11}$, $S_{OA12}$, stream $S_{OA1}$ before separation thereof into $S_{OA11}$, $S_{OA12}$ to the crude product $RP_C$.

In addition crude product $RP_C$ may also be passed through an intermediate evaporator $V_{ZC}$ or a bottoms evaporator $V_{SC}$ and in $V_{ZC}/V_{SC}$ energy, preferably heat, may be transferred from at least a portion of a stream selected from $S_{OA1}$, $S_{OA2}$ to the crude product $RP_C$.

In addition the bottoms product stream $S_{CP}$ may also be partially passed through an intermediate evaporator $V_{SC}$ and then partially recycled to $RR_C$, wherein in $V_{SC}$ energy, preferably heat, is transferred from at least a portion of a stream selected from $S_{OA1}$, $S_{OA2}$ to the recycled portion of $S_{CP}$ and then in the column $RR_C$ transferred from $S_{CP}$ to the crude product $RP_C$ present in the column.

The transfer of energy from at least a portion of a stream selected from $S_{OA1}$, $S_{OA2}$ to the recited streams is effected directly or indirectly, i.e. without or with heat transfer medium $W_1$, as described accordingly in section 4.1.4.

The preferred embodiment of the process according to the invention makes it possible to efficiently employ the energy from $S_{OA1}$, $S_{OA2}$, in particular from $S_{OA2}$, $S_{OA11}$, $S_{OA12}$. This reduces the total energy demand.

5. EXAMPLES

5.1 Example 1 (Noninventive), Corresponds to FIG. 1

A stream of aqueous NaOH (50% by weight) $S_{AE2}$ <102> of 100 kg/h is supplied at 30° C. to the top of a reaction column $RR_A$ <100>. A vaporous methanol stream $S_{AE1}$ <103> of 1034.9 kg/h is supplied in countercurrent at the bottom of the reaction column $RR_A$ <100>. The reaction column $RR_A$ <100> is operated at a head pressure of 2.15 bar abs. At the bottom of the column $RR_A$ <100> a virtually water-free product stream $S_{AP*}$ <104> of 219.7 kg/h is withdrawn (30% by weight sodium methoxide in methanol). The evaporator $V_{SA}$ <105> of the reaction column $RR_A$ <100> introduces about 24 KW of heating power using low pressure steam. A vaporous methanol-water stream $S_{AB}$ <107> is withdrawn at the top of the reaction column $RR_A$ <100> and 80 kg/h thereof are condensed in the condenser $K_{RRA}$ <108> and returned to the reaction column $RR_A$ <100> as reflux while the remaining stream of 915.2 kg/h is supplied to a rectification column $RD_A$ <300>. The rectification column $RD_A$ <300> is operated at a head pressure of 2.0 bar abs. At the bottom of the rectification column $RD_A$ <300> a liquid water stream $S_{UA}$ <304> of 72.2 kg/h is discharged (500 ppmw of methanol). At the top of the rectification column $RD_A$ <300> a vaporous methanol stream $S_{OA}$ <302> (2 bar, 83° ° C.; 200 ppmw of water) of 1903.6 kg/h is withdrawn and 63.9 kg/h thereof are condensed in a condenser $K_{RD}$ <407> while the remaining stream is supplied to a first compressor $VD_{AB2}$ <303> and therein compressed to 2.6 bar abs. The stream is subsequently divided and a stream of 1034.9 kg/h is recycled to the reaction column $RR_A$ <100>. The remainder of 804.8 kg/h is supplied to a multi-stage compression with intermediate cooling. In the compressor $V_{D1}$ <401> the stream is compressed to $p_{OA1}$=4.8 bar abs. and $T_{OA1}$=156° C. to obtain stream <403>. In the subsequent intermediate cooling in the intermediate cooler $WT_X$ <402> the stream is cooled to 145° C. and about 4.4 KW of heat are removed using cooling water. In the compressor $VD_x$ <405> the stream is finally compressed again to 9.0 bar and 200° C. to obtain stream <404>. The subsequent condenser which is simultaneously the bottoms evaporator $V_{SRD}$ <406> of the rectification column $RD_A$ <300> provides the approximately 238 KW of heating power for the rectification column $RD_A$ <300>. The thus condensing methanol stream <404> is mixed together with 191.9 kg/h of fresh methanol (1000 ppmw of water) <408> and the 63.9 kg/h of previously condensed vapours and recycled to the top of the rectification column $RD_A$ <300>.

The compressor power sums to about 55 kW.

Together with the 24 KW for the heating steam this results in a compressor and heating steam power demand of about 79 kW.

5.2 Example 2 (Noninventive), Corresponds to FIG. 2

The arrangement in noninventive example 2 corresponds to that of example 1 with the following differences:

The rectification column $RD_A$ <300> comprises an intermediate evaporator $V_{ZRD}$ <409>. A liquid stream $S_{ZA}$ <305> is withdrawn from the rectification column $RD_A$ <300> at 94° C. and about 230 KW of heat are transferred thereto in the intermediate evaporator $V_{ZRD}$ <409>, wherein the stream is partially evaporated and subsequently returned to the rectification column $RD_A$ <300>. A vaporous methanol stream $S_{OA}$ <302> (200 ppmw of water) of 1887.1 kg/h is withdrawn at the top of the rectification column $RD_A$ <300> and 89.4 kg/h thereof are condensed in a condenser $K_{RD}$ <407>. The remaining stream is compressed to 2.6 bar abs. in a first compressor $VD_{AB2}$ <303> as in example 1. A substream of 1034.9 kg/h is then recycled to the reaction column $RR_A$ <100>. The remainder of 762.8 kg/h is compressed to 5.6 bar abs. and 168° C. to obtain stream <403>. The subsequent condenser which is simultaneously the intermediate evaporator $V_{SRD}$ <409> of the rectification column $RD_A$ <300> provides the approximately 230 KW of heating power for the rectification column $RD_A$ <300>. The thus condensed methanol stream <403> is mixed with 191.9 kg/h of fresh methanol <408> and the 89.4 kg/h of previously condensed vapours and returned to the top of the rectification column $RD_A$ <300>. The bottoms evaporator $V_{SRD}$ <406> of the reaction column $RD_A$ <300> introduces about 20 KW of heating power using low pressure steam. Compared to example 1 the vapour stream need be compressed only to 5.6 bar abs. instead of 9 bar abs. to be able to transmit its heat to the evaporator $V_{ZRD}$ <409> since the boiling temperature in the intermediate evaporator $V_{ZRD}$ <409> is lower than in the bottoms evaporator $V_{SRD}$ <406>. The compressor power thus sums to only about 38 KW (instead of 55 KW) while the heating steam demand increases relative to example 1 to about 44 KW since the bottoms evaporator $V_{SRD}$ <406> requires a heating power of 20 KW and this introduced with the heat of low pressure steam. The compressor and heating steam power demands thus sum to about 82 kW.

5.3 Example 3 Inventive), Corresponds to FIG. 3

The arrangement in inventive example 3 corresponds to that of example 1 and 2 with the following differences:

A vaporous methanol stream $S_{OA}$ <302> (200 ppmw of water) of 1898.9 kg/h is withdrawn at the top of the rectification column $RD_A$ <300> and 33.9 kg/h thereof are condensed in a condenser $K_{RD}$ <407>. The remaining stream is compressed to 2.6 bar abs. in a first compressor $VD_{AB2}$ <303> as in example 2 and subsequently a substream of 1034.9 kg/h is recycled to the reaction column $RR_A$ <100>. The remainder of 830.1 kg/h is initially compressed to 5.6 bar abs. and 169° C. to obtain stream $S_{OA1}$ <403>. A portion $S_{OA11}$ <4031> (761.7 kg/h) of this stream is passed into a downstream condenser which is simultaneously the intermediate evaporator $V_{ZRD}$ <409> of the rectification column $RD_A$ <300> and provides about 230 KW of heating power for the rectification column $RD_A$ <300>. The other portion $S_{OA12}$ <4032> (68.4 kg/h) is subsequently cooled to about 154° C. in an intermediate cooling in intermediate cooler $WT_X$ <402> wherein about 0.5 KW of heat are removed via cooling water. The stream $S_{OA12}$ <4032> is subsequently compressed in a further compressor $VD_x$ <405> to obtain stream $S_{OA2}$ <404> having $p_{OA2}$=9.0 bar and $T_{OA}2$=196° C. The subsequent condenser which is simultaneously the bottoms evaporator $V_{SRD}$ <406> of the rectification column $RD_A$ <300> provides about 20 KW of heating power for the rectification column $RD_A$ <300>. The methanol streams $S_{OA11}$ <4031> and $S_{OA2}$ <404> condensed in the intermediate and bottoms evaporators $V_{ZRD}$ <409> and $V_{SRD}$ <406> are mixed with 191.9 kg/h of fresh methanol <408> and the 33.9 kg/h of previously condensed vapours and returned to the top of the rectification column $RD_A$ <300>.

The compressor power sums to about 42 KW (instead of 55 KW in example 1). Since no low pressure steam is required for the bottoms evaporator $V_{SRD}$ <406> only about 24 KW need be provided using heating steam as in example 1. The sum of the compressor and heating steam power demands thus falls to about 66 kW.

Compared to example 1 only a lower vapour stream need be compressed to 9 bar abs., a large part of the vapour stream need only be compressed to 5.6 bar abs. as in example 2, thus reducing the total compressor power. However, compared to example 2 steady state operation does not require any low pressure steam in the bottoms evaporator $V_{SRD}$ <406>, thus reducing the heating steam demand compared to example 2.

The total energy to be supplied is minimized by the process according to example 3.

The proportion of heating power provided by low pressure steam and compressor power in each case is shown in FIG. 9.

Result: The inventive procedure of effecting staged compression of the vapour stream and thus operating the intermediate evaporator and the bottoms evaporator with the vapours compressed to different extents surprisingly achieves energy savings.

The invention claimed is:

1. A process for producing at least one alkali metal alkoxide of formula $M_AOR$, wherein R is methyl, and wherein $M_A$ is a metal selected from sodium and potassium, wherein:

(α1) a reactant stream $S_{AE1}$ comprising ROH is reacted with a reactant stream $S_{AE2}$ comprising $M_AOH$ in countercurrent in a reactive rectification column $RR_A$ to produce a crude product $RP_A$ comprising $M_AOR$, water, ROH, and $M_AOH$;

wherein a bottoms product stream $S_{AP}$ comprising ROH and $M_AOR$ is withdrawn at the lower end of $RR_A$ and a vapour stream $S_{AB}$ comprising water and ROH is withdrawn at the upper end of $R_{RA}$;

(β) at least a portion of the vapour stream $S_{AB}$ is employed as mixture G in step (a) of a process for workup of a mixture G comprising water and alcohol ROH;

wherein in the process for workup of a mixture G:

(a) the mixture G is passed into a rectification column $RD_A$ and in $RD_A$ is separated into at least one vapour stream $SO_A$ comprising ROH which is withdrawn at the upper end of $RD_A$ and at least one stream $S_{UA}$ comprising water which is withdrawn at the lower end of $RD_A$;

(b) at least one side stream $S_{ZA}$ is withdrawn from $RD_A$ and recycled to $RD_A$;

(c) at least a portion of $S_{OA}$ is compressed to afford a vapour stream $S_{OA1}$ which is compressed relative to $S_{OA}$;

(d) energy is transferred from a first portion $S_{OA11}$ of the compressed vapour stream $S_{OA1}$ to $S_{ZA}$ before $S_{ZA}$ is recycled to $RD_A$;

(e) a portion $S_{OA12}$ of the compressed vapour stream $S_{OA1}$ that is distinct from $S_{OA11}$ is subjected to further compression to produce a vapour stream $S_{OA2}$ that is compressed relative to $S_{OA11}$;

(f) energy is transferred from at least a portion of $S_{OA2}$ to at least a portion $S_{UA1}$ of $S_{UA}$ before $S_{UA1}$ is recycled to $RD_A$.

2. The process of claim 1, wherein in step (d), energy is transferred from $S_{OA11}$ to $S_{ZA}$ in an intermediate evaporator $V_{ZRD}$.

3. The process of claim 1, wherein, in step (f), energy is transferred from at least a portion of $S_{OA2}$ to the at least a portion $S_{UA1}$ of $S_{UA}$ in a bottoms evaporator $V_{SRD}$.

4. The process of claim 1, wherein, once energy has been transferred from $S_{OA11}$ to $S_{ZA}$ according to step (d), energy is transferred from $S_{OA11}$ to $S_{OA}$ and/or once energy has been transferred from at least a portion of $S_{OA2}$ to the at least a portion $S_{UA1}$ of $S_{UA}$ according to step (f), energy is transferred from at least a portion of $S_{OA2}$ to $S_{OA}$.

5. The process of claim 1, wherein rectification column $RD_A$ and reaction column $RR_A$ are accommodated in one column shell, wherein the columns are at least partially separated from one another by a dividing wall extending to the bottom of the column.

6. The process of claim 1, wherein a portion of $S_{OA}$ is employed as reactant stream $S_{AE1}$ in step (α1).

7. The process of claim 1, wherein energy is transferred from at least a portion of a stream selected from $S_{OA1}$ and $S_{OA2}$ to the crude product $RP_A$.

8. The process of claim 1, wherein, in a reactive rectification column $RR_C$, a reactant stream $S_{CE1}$ comprising $M_cOR'$ is reacted in countercurrent with a reactant stream $S_{CE2}$ comprising R"OH to produce a crude product $RP_C$ comprising $M_COR"$ and R'OH;

wherein a bottoms product stream $S_{CP}$ comprising $M_COR"$ is withdrawn at the lower end of $RR_C$ and a vapour stream $S_{CB}$ comprising R'OH is withdrawn at the upper end of $RR_C$;

and wherein R' and R" are two distinct $C_1$ to $C_6$ hydrocarbon radicals and $M_C$ is a metal selected from sodium and potassium;

and wherein energy is transferred from at least a portion of a stream selected from $S_{OA1}$ and $S_{OA2}$ to the crude product $RP_C$.

9. A process for producing at least one alkali metal alkoxide of formula $M_AOR$, wherein R is methyl, and wherein $M_A$ is a metal selected from sodium, potassium, wherein:

(α1) a reactant stream $S_{AE1}$ comprising ROH is reacted with a reactant stream $S_{AE2}$ comprising $M_AOH$ in countercurrent in a reactive rectification column $RR_A$ to produce a crude product $RP_A$ comprising $M_AOR$, water, ROH, $M_AOH$;

wherein a bottoms product stream $S_{AP}$ comprising ROH and $M_AOR$ is withdrawn at the lower end of $RR_A$ and a vapour stream $S_{AB}$ comprising water and ROH is withdrawn at the upper end of $RR_A$;

(α2) simultaneously with and spatially separate from step (α1), a reactant stream $S_{BE1}$ comprising ROH is reacted with a reactant stream $S_{BE2}$ comprising $M_BOH$ in countercurrent in a reactive rectification column $RR_B$ to afford a crude product $RP_B$ comprising $M_BOR$, water, ROH, $M_BOH$, wherein $M_B$ is a metal selected from sodium and potassium;

wherein a bottoms product stream $S_{BP}$ comprising ROH and $M_BOR$ is withdrawn at the lower end of $RR_B$ and a vapour stream $S_{BB}$ comprising water and ROH is withdrawn at the upper end of $RR_B$;

(β) at least a portion of the vapour stream $S_{AB}$, and at least a portion of the vapour stream $S_{BB}$, in admixture with $S_{AB}$ or separate from $S_{AB}$, is employed as mixture G in step (a) of a process for workup of a mixture G comprising water and alcohol ROH;

wherein in the process for workup of a mixture G:

(a) the mixture G is passed into a rectification column $RD_A$ and in $RD_A$ is separated into at least one vapour stream $S_{OA}$ comprising ROH which is withdrawn at the upper end of $RD_A$ and at least one stream $S_{UA}$ comprising water which is withdrawn at the lower end of $RD_A$;

(b) at least one side stream $S_{ZA}$ is withdrawn from $RD_A$ and recycled to $RD_A$;

(c) at least a portion of $S_{OA}$ is compressed to afford a vapour stream $S_{OA1}$ which is compressed relative to $SO_A$;

(d) energy is transferred from a first portion $S_{OA11}$ of the compressed vapour stream $S_{OA1}$ to $S_{ZA}$ before $S_{ZA}$ is recycled to RDA;

(e) a portion $S_{OA12}$ of the compressed vapour stream $S_{OA1}$ that is distinct from $S_{OA11}$ is subjected to further compression to produce a vapour stream $S_{OA2}$ that is compressed relative to $S_{OA11}$;

(f) energy is transferred from at least a portion of $S_{OA2}$ to at least a portion $S_{UA1}$ of $S_{UA}$ before $S_{UA1}$ is recycled to RDA.

10. The process of claim 9, wherein in step (d), energy is transferred from $S_{OA11}$ to $S_{ZA}$ in an intermediate evaporator $V_{ZRD}$.

11. The process of claim 9, wherein in step (f), energy is transferred from at least a portion of $S_{OA2}$ to the at least a portion $S_{UA1}$ of $S_{UA}$ in a bottoms evaporator $V_{SRD}$.

12. The process of claim 9, wherein once energy has been transferred from $S_{OA11}$ to SZA according to step (d), energy is transferred from $S_{OA11}$ to $S_{OA}$ and/or once energy has been transferred from at least a portion of $S_{OA2}$ to the at least a portion $S_{UA1}$ of $S_{UA}$ according to step (f) energy is transferred from at least a portion of $S_{OA2}$ to SOA.

13. The process of claim 9, wherein at least two of the columns selected from rectification column $RD_A$, reaction column $RR_A$ and reaction column $RR_B$ are accommodated in one column shell, wherein the columns are at least partially separated from one another by a dividing wall extending to the bottom of the column.

14. The process of claim 9, wherein a portion of $S_{OA}$ is employed as reactant stream $S_{AE1}$ in step (α1) and alternatively or in addition as reactant stream $S_{BE1}$ in step (α2).

15. The process of claim 9, wherein energy is transferred from at least a portion of a stream selected from $S_{OA1}$ and $S_{OA2}$ to the crude product $RP_A$ and alternatively or in addition to the crude product $RP_B$.

16. The process of claim 9, wherein in a reactive rectification column $RR_C$ a reactant stream $S_{CE1}$ comprising $M_COR'$ is reacted in countercurrent with a reactant stream $S_{CE2}$ comprising R"OH to produce a crude product $RP_C$ comprising $M_COR"$ and R'OH;

wherein a bottoms product stream $S_{CP}$ comprising $M_COR"$ is withdrawn at the lower end of $RR_C$ and a vapour stream $S_{CB}$ comprising R'OH is withdrawn at the upper end of $RR_C$;

and wherein R' and R" are two distinct $C_1$ to $C_6$ hydrocarbon radicals and $M_C$ is a metal selected from sodium and potassium;

and wherein energy is transferred from at least a portion of a stream selected from $S_{OA1}$ and $S_{OA2}$ to the crude product RPC.

17. The process of claim 16, wherein R'=methyl.

18. The process of claim 17, wherein the process produces $S_{AP}$, wherein R=methyl and wherein at least a portion of $S_{AP}$ is employed as $S_{CE1}$.

19. The process of claim 17, wherein the process produces SBP, wherein R=methyl and wherein at least a portion of $S_{BP}$ is employed as $S_{CE1}$.

20. The process of claim 17, wherein R"=ethyl.

* * * * *